(12) United States Patent　　　(10) Patent No.:　US 12,642,658 B2
　　　Troxell et al.　　　　　　　　　(45) Date of Patent:　Jun. 2, 2026

(54) SMART IMPLANTS FOR PERIPROSTHETIC JOINT INFECTION

(71) Applicant: GLOBUS MEDICAL, INC., Audubon, PA (US)

(72) Inventors: Paden Troxell, Conshohocken, PA (US); David C. Paul, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 341 days.

(21) Appl. No.: 18/455,741

(22) Filed: Aug. 25, 2023

(65) Prior Publication Data

US 2025/0065113 A1　　Feb. 27, 2025

Related U.S. Application Data

(63) Continuation of application No. 18/455,696, filed on Aug. 25, 2023.

(51) Int. Cl.
| | |
|---|---|
| *A61F 2/30* | (2006.01) |
| *A61B 5/00* | (2006.01) |
| *A61F 2/48* | (2006.01) |
| *A61N 1/08* | (2006.01) |
| *A61N 1/32* | (2006.01) |
| *A61F 2/38* | (2006.01) |

(52) U.S. Cl.
CPC .............. *A61F 2/30* (2013.01); *A61B 5/0031* (2013.01); *A61B 5/412* (2013.01); *A61B 5/4528* (2013.01); *A61B 5/4839* (2013.01); *A61F 2/482* (2021.08); *A61N 1/08* (2013.01);

*A61N 1/32* (2013.01); *A61F 2002/30668* (2013.01); *A61F 2/3877* (2013.01)

(58) Field of Classification Search
CPC ..... A61B 5/4851; A61B 5/0031; A61B 5/686; A61B 5/057; A61B 5/4839; A61F 2/482; A61N 1/08
See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |

(Continued)

OTHER PUBLICATIONS

US 8,231,638 B2, 07/2012, Swarup et al. (withdrawn)

*Primary Examiner* — Joseph M Dietrich

(57)　　　　　ABSTRACT

A medical implant includes an implant component configured to be implanted in a patient, an electrode array, an energy storage device, a wireless communication interface, and implant circuitry. The electrode array includes sensor electrodes spaced apart on the implant component. The energy storage device, wireless communication interface, and implant circuitry are inside the implant component. The wireless communication interface is configured to communicate with a wireless receiver that is separate from the medical implant. The implant circuitry is operative to supply voltage to at least one of the sensor electrodes to measure electrical and/or chemical characteristics associated with when a biofilm is forming on the implant component, and communicate signaling indicating the electrical and/or chemical characteristics through the wireless communication interface.

17 Claims, 20 Drawing Sheets

(56)                References Cited

U.S. PATENT DOCUMENTS

| | | | |
|---|---|---|---|
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |

(56) References Cited

U.S. PATENT DOCUMENTS

| | | | |
|---|---|---|---|
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |

(56) References Cited

U.S. PATENT DOCUMENTS

| | | |
|---|---|---|
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |

(56)  References Cited

U.S. PATENT DOCUMENTS

| | | |
|---|---|---|
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |

(56) References Cited

U.S. PATENT DOCUMENTS

| | | | |
|---|---|---|---|
| 2014/0171781 A1 | 6/2014 | Stiles | |
| 2014/0171900 A1 | 6/2014 | Stiles | |
| 2014/0171965 A1 | 6/2014 | Loh et al. | |
| 2014/0180308 A1 | 6/2014 | von Grunberg | |
| 2014/0180309 A1 | 6/2014 | Seeber et al. | |
| 2014/0187915 A1 | 7/2014 | Yaroshenko et al. | |
| 2014/0188132 A1 | 7/2014 | Kang | |
| 2014/0194699 A1 | 7/2014 | Roh et al. | |
| 2014/0221819 A1 | 8/2014 | Sarment | |
| 2014/0222023 A1 | 8/2014 | Kim et al. | |
| 2014/0228631 A1 | 8/2014 | Kwak et al. | |
| 2014/0234804 A1 | 8/2014 | Huang et al. | |
| 2014/0257328 A1 | 9/2014 | Kim et al. | |
| 2014/0257329 A1 | 9/2014 | Jang et al. | |
| 2014/0257330 A1 | 9/2014 | Choi et al. | |
| 2014/0275760 A1 | 9/2014 | Lee et al. | |
| 2014/0275985 A1 | 9/2014 | Walker et al. | |
| 2014/0276931 A1 | 9/2014 | Parihar et al. | |
| 2014/0276940 A1 | 9/2014 | Seo | |
| 2014/0276944 A1 | 9/2014 | Farritor et al. | |
| 2014/0288413 A1 | 9/2014 | Hwang et al. | |
| 2014/0299648 A1 | 10/2014 | Shelton, IV et al. | |
| 2014/0303434 A1 | 10/2014 | Farritor et al. | |
| 2014/0303643 A1 | 10/2014 | Ha et al. | |
| 2014/0305995 A1 | 10/2014 | Shelton, IV et al. | |
| 2014/0309659 A1 | 10/2014 | Roh et al. | |
| 2014/0316436 A1 | 10/2014 | Bar et al. | |
| 2014/0323803 A1 | 10/2014 | Hoffman et al. | |
| 2014/0324070 A1 | 10/2014 | Min et al. | |
| 2014/0330288 A1 | 11/2014 | Date et al. | |
| 2014/0364720 A1 | 12/2014 | Darrow et al. | |
| 2014/0371577 A1 | 12/2014 | Maillet et al. | |
| 2015/0039034 A1 | 2/2015 | Frankel et al. | |
| 2015/0085970 A1 | 3/2015 | Bouhnik et al. | |
| 2015/0146847 A1 | 5/2015 | Liu | |
| 2015/0150524 A1 | 6/2015 | Yorkston et al. | |
| 2015/0196261 A1 | 7/2015 | Funk | |
| 2015/0213633 A1 | 7/2015 | Chang et al. | |
| 2015/0335480 A1 | 11/2015 | Alvarez et al. | |
| 2015/0342647 A1 | 12/2015 | Frankel et al. | |
| 2016/0005194 A1 | 1/2016 | Schretter et al. | |
| 2016/0166329 A1 | 6/2016 | Langan et al. | |
| 2016/0235480 A1 | 8/2016 | Scholl et al. | |
| 2016/0249990 A1 | 9/2016 | Glozman et al. | |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0202629 A1 | 7/2017 | Maillet et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0231710 A1 | 8/2017 | Scholl et al. | |
| 2017/0258426 A1 | 9/2017 | Risher-Kelly et al. | |
| 2017/0273748 A1 | 9/2017 | Hourtash et al. | |
| 2017/0296277 A1 | 10/2017 | Hourtash et al. | |
| 2017/0360493 A1 | 12/2017 | Zucher et al. | |
| 2019/0060556 A1* | 2/2019 | Huiszoon | A61M 5/001 |
| 2024/0148328 A1* | 5/2024 | Fedon | A61B 5/0538 |

* cited by examiner

320

330

340

100

Electrode
Array 300

Electrodes
310

*Fig. 3*

Reference
Electrode
420

Working
Electrode
410a

Working
Electrode
410b

Counter
Electrode
430

Working
Electrode
410n

Working
Electrode
410c

Reference Electrode 420
Working Electrode 410a
Working Electrode 410b
Counter Electrode 430
Working Electrode 410n
Working Electrode 410c Bacteria 1
Bacteria 2
Bacteria 3

Reference Electrode 420
Oxygen Sensor 510a
Impedance Sensor 510b
Counter Electrode 430
pH Sensor 510c Oxygen
Impedance
pH

Fig. 6

SMART IMPLANTS FOR PERIPROSTHETIC JOINT INFECTION

CROSS REFERENCE TO RELATED APPLICATIONS

The present application is a continuation of U.S. patent application Ser. No. 18/455,696, filed on Aug. 25, 2023, which is incorporated herein by reference

FIELD

The present disclosure relates to medical implants, such as for joint arthroplasty.

BACKGROUND

Periprosthetic joint infection (PJI) is one of the most feared complications in joint arthroplasty due to the ineffectiveness of antibiotics, invasive treatment options, and relatively high annual mortality rate of 4%. If caught early enough, antibiotics and natural immune responses are very effective at intercepting the free-floating bacteria within the surgical site. However, antibiotics are remarkably ineffective at eradicating bacteria within biofilm on the surface of the implant.

Biofilm develops as bacteria adhere to and colonize on the surface of an implant. The biofilm layer serves as a biochemical fortress that prevents penetration of antibiotic agents. It has been reported that 500-5000 times the concentration of antibiotics are required to have the same effectiveness on biofilm bacteria as compared to free-floating planktonic bacteria. As a result, the most common treatment for PJI is highly invasive two-stage revision.

Two-stage revision involves an initial operation to remove the septic implant and debride the surgical site and a second procedure to place new implant components. Although two-stage revision is the most common treatment option for PJI, the success rate has been reported to be only 85%. In addition, the risk of reinfection following revision for PJI has been reported to be 9% compared to 1-2% following the primary procedure. Also, the annual mortality rate has been reported to be as high as 14% following two-stage revision.

Much of the research and product development activity has been focused on preventing, rather than treating, infection following joint arthroplasty. Despite the incorporation of prevention strategies, including sterilization standards, shorter operative times, laminar airflow systems, body exhaust suits, perioperative antibiotics, antibiotic cement, and antimicrobial adhesive dressings, the incidence of PJI after THA and TKA has remained relatively constant over the past 20 years. This lack of improvement is likely due in part to the ineffectiveness of these solutions in preventing, detecting, and eradicating the pathogenesis of joint infection, which is the formation of biofilm.

SUMMARY

Embodiments of the present disclosure are directed to smart joint reconstruction implants that can provide physicians/clinicians and their patients the ability to monitor, detect, and diagnose PJI. These implants could also operate to detect and eradicate PJI, which may increase the effectiveness of antibiotics and reduce the prevalence of two-stage revision procedures.

Some embodiments of the present disclosure are directed to a medical implant that includes an implant component configured to be implanted in a patient, an electrode array with sensor electrodes spaced apart on the implant component, an energy storage device within the implant component, a wireless communication interface within the implant component, and implant circuitry within the implant component. The wireless communication interface is configured to communicate with a wireless receiver that is separate from the medical implant. The implant circuitry is operative to supply voltage to at least one of the sensor electrodes to measure electrical and/or chemical characteristics associated with when a biofilm is forming on the implant component, and communicate signaling indicating the electrical and/or chemical characteristics through the wireless communication interface.

Some other embodiments are directed to a corresponding computing device that includes a wireless communication interface and circuitry. The wireless communication interface is operative to receive, from a medical implant, signaling based on a measured electrical and/or chemical characteristics through sensor electrodes spaced apart on a component of the medical implant. The circuitry is operative to detect presence of a biofilm and a location of the biofilm on the medical implant based on the received signaling, and transmit a message that identifies stimulation electrodes, that are associated with the determined location of the biofilm, on the component of the medical implant that are to be stimulated by current supplied by implant circuitry at a level which reduces the biofilm.

Possible advantages that may be provided by one or one of these and other embodiments disclosed herein may include active prevention, early detection, and non-invasive eradiation of biofilm/bacteria. One or more of the embodiments may reduce the incidence of early postoperative infections by preventing development of biofilm and forcing the bacteria to remain free-floating, where it is vulnerable to natural immune responses and antibiotics. Additionally, the embodiment(s) may monitor the formation of biofilm to provide early detection of late chronic PJI and feedback on the effectiveness of treatment. The embodiment(s) may also provide a treatment option to increase the effectiveness of antibiotics and reduce the need for 2-stage revisions. If an infection is detected, either through the onset of symptoms or measured biofilm, an eradication modality can be utilized to directly kill adhered bacteria, detach the biofilm layer, and expel bacteria into the surrounding synovial fluid where can be intercepted by accompanying antibiotics.

Other medical implants, computing devices, and corresponding methods according to embodiments of the present disclosure will be or become apparent to one with skill in the art upon review of the following drawings and detailed description. It is intended that all such additional medical implants, computing devices, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIG. 3 illustrates a front view of the medical implant which includes a magnified view of one of the electrode arrays of the implant component, according to some embodiments of the present disclosure;

FIG. 6 illustrates a view of the electrode array with biofilm built up on the electrode array, and the electrode array is divided into sets and zones of electrodes, according to some embodiments of the present disclosure;

DETAILED DESCRIPTION

Figure 1A:
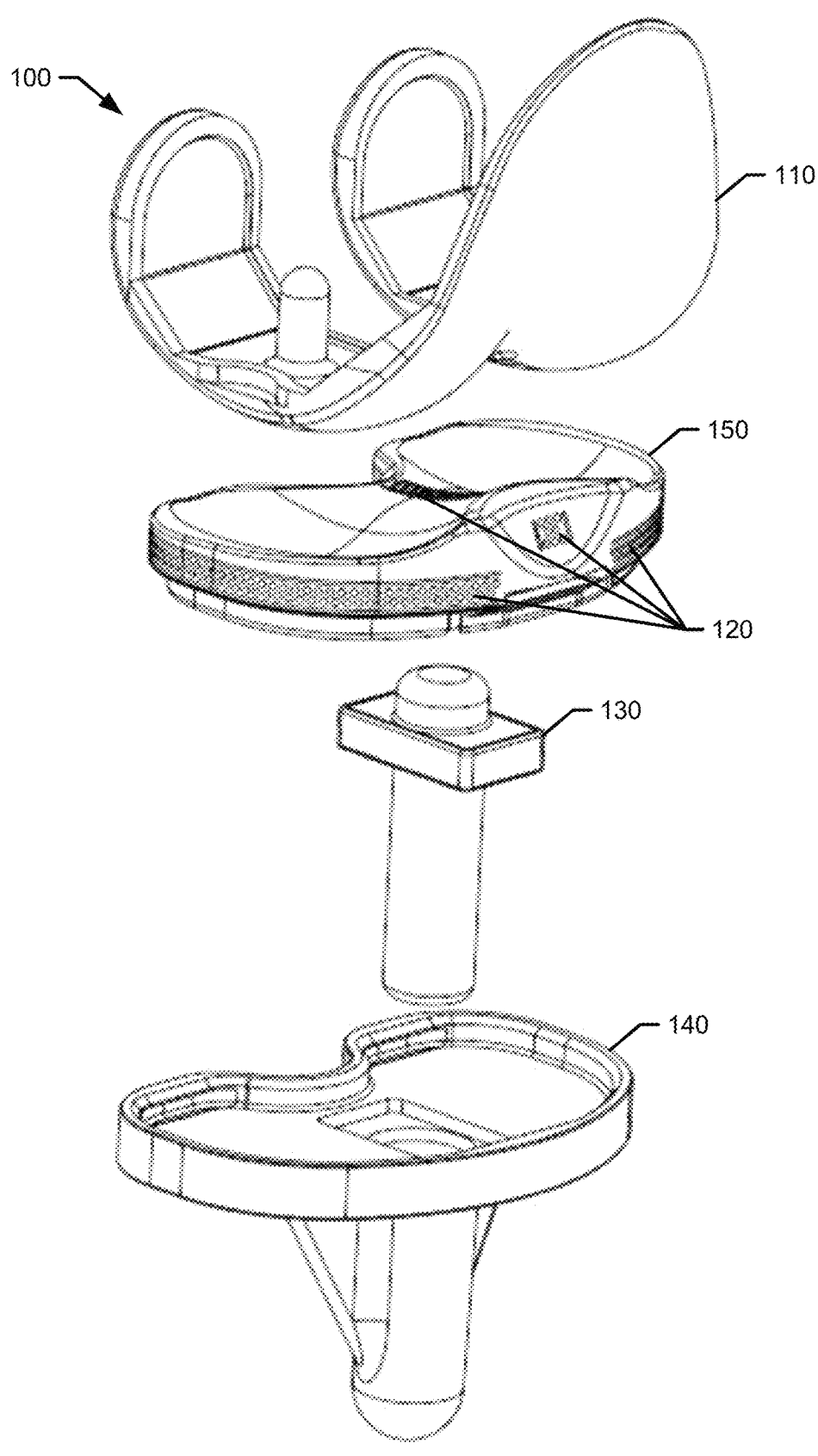
FIG. 1A illustrates an exploded isometric view of some components of a medical implant including a tibial insert, implant component, energy storage device, and tibial tray according to some embodiments of the present disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to joint reconstruction implants that have electronic circuits ("smart implants") which are operate to provide physicians and/or their patients the operational ability to prevent, monitor, detect, and diagnose Periprosthetic Joint Infection (PJI). Smart implants can be further operative to reduce or prevent and eradicate PJI through operation of the electronic circuits, and may increase the effectiveness of antibiotics and reduce the prevalence of two-stage revision procedures.

FIG. 1A illustrates an exploded isometric view of some components of a medical implant 100 including a tibial insert 110, implant component 150, energy storage device 130, and tibial tray 140 according to some embodiments of the present disclosure.

Referring to FIG. 1A, the medical implant 100 is a knee replacement implant. The implant component 150 may be housed between the tibial tray 140 and tibial insert 110 within cavities in each component. FIG. 1A is an implant construct for total knee arthroplasty, however, it should be noted that the present disclosure is directed to various embodiments in any orthopedic implant application including but not limited to partial knee arthroplasty, revision knee arthroplasty, total hip arthroplasty, intramedullary nailing, trauma plating, and spinal fusion.

The implant component 150 of the medical implant 100 may include at least one electrode array (e.g., electrode arrays 120) that is exposed to fluid and/or tissue of a patient that the medical implant is implanted in. For example, the implant component 150 includes two electrode arrays along the side of the implant component 150, a third electrode array on top of the implant component 150 that is facing upward, and a fourth electrode array that is towards the front of the implant component 150 and is facing in a tilted forward facing direction. While embodiments illustrate and describe specific placements of the electrode arrays, embodiments herein are not limited to such placements and can be on any surface of the medical implant 100 such as the implant component 150, tibial insert 110, and/or tibial tray 140. In preferred embodiments, the electrode arrays are placed in locations where there is minimal or no articular wear from the different components of the medical implant. For example, in locations where the different components of the medical implant do not contact each other while implanted in the patient.

The electrode arrays 120 may include at least two electrodes spaced apart on the implant component 150. In some embodiments, at least one of the electrodes is a sensor electrode that is configured to measure electrical and/or chemical characteristics. In some embodiments, the electrical and/or chemical characteristics indicate at least one of impedance, conductivity, temperature, oxygen, and potential hydrogen (pH).

In some embodiments, pH is measured by the working electrode(s) by measuring the change in pH level to obtain qualitative assessment of biofilm and its growth. For example, a voltage signal may be generated in response to change in the pH as biofilm grows. As biofilm grows, the biofilm may produce more pH byproducts. If the biofilm produces more acidic by products, this may lower the pH and provide a lower voltage response. If the biofilm produces more basic byproducts, this may increase the pH and provides a higher voltage response. If the biofilm produces both acidic and basic byproducts, this may alter the pH level based on the more dominant byproduct present and provide the respective voltage response.

In some embodiments, oxygen is measured by the working electrode(s) by a change in oxygen levels/concentrations to obtain qualitative assessment of the biofilm and its growth. For example, a current signal may be generated in response to change in oxygen level/concentrations as the biofilm grows. As the biofilm grows more oxygen molecules may be consumed by the bacteria for their metabolic processes. The extracellular matrix of the biofilm may become dense and thick and the pathways where the oxygen molecules travel becomes narrower making it harder for oxygen to travel to inner deep layers of the biofilm's medium. This may result in a depletion of oxygen molecules in the inner layers and most oxygen molecules may stay on the surface of biofilm's medium. With less available oxygen molecules in the inner layers of the extracellular matrix, there may be less redox reactions happening since redox reactions requires oxygen molecules. Redox reactions are reactions that involve transfer and movement of electrons between the biofilm and the working electrode. Less redox reactions may result in less electron transfer, which yields less electrical current flow in the system since electrical current is based on the rate of electric charges.

In some embodiments, conductivity is measured by the working electrode(s) by a change in conductivity to obtain quantitative assessment of biofilm and its growth. For example, a current signal is generated in response to change in conductivity as biofilm grows. As the biofilm grows, the biofilm may produce more extra polymeric substances (EPS) which enhances the conductive properties of biofilm's medium. This is due to proteins and other compounds that form this matrix of EPS, may create some conductive network within the biofilm's medium. This may result in the allowance for more movement of electrons. With more of these substances, the extracellular matrix can become more conductive, which increases the electrical current. It may depend on whether we have more of these conductive pathways being created or more of a complex structure with densely packed cells and thick extracellular matrix that acts as barrier to prevent electron flow, being created.

In some embodiments, impedance is measured by the working electrode(s) as a change in impedance, reflected as change in voltage corresponding to bacterial cell sizes to obtain quantitative assessment of biofilm and its growth. For example, a voltage signal is generated in response to the size of bacterial cells passing through the aperture that will alter the impedance as biofilm grows. As biofilm grows, the biofilm may produce more and/or larger biofilm particles such as bacterial cells that will enter through the aperture (that is designed to allow only biofilm particles to enter through while blocking out any fluid). As those charged particles (the bacterial cells) flows through the aperture and occupy the channels, they will disrupt and interrupt the flow of fluid (synovial or electrolyte solution) that was supposed to originally fill the channel in the first place. This obstruction/displacement of fluid in the channels may alter the impedance of the electrode array. This change in impedance may be detected/reflected as change in voltage across the electrode array where the magnitude of the voltage change corresponds to the size or concentration of the particles, which are the bacterial cells that entered through the aperture. Larger size and/or higher number (concentration) of particles/bacterial cells entering the aperture, as a result of increased biofilm growth may yield more impedance which translates to larger voltage change. Therefore, larger magnitude of voltage change may correspond to larger bacterial cell size and/or more concentration of it, which can be counted and quantified.

In some embodiments, the working electrode(s) act as temperature sensor or have temperature sensors connected thereto, in order to measure the temperature of the fluid/tissue in contact with the working electrode(s).

In some embodiments, the electrode arrays 120 are located on the surface of parts of the medical implant 100. In other embodiments, the electrode arrays 120 are embedded on the surface of components of the medical implant 100 and have at least two electrodes exposed to allow measuring of electrical and/or chemical characteristics.

In some embodiments, the medical implant 100 may include implant circuitry inside the implant component 150 that is operative to supply voltage to at least one of the sensor electrodes to measure electrical and/or chemical characteristics, and communicate signaling indicating the electrical and/or chemical characteristics through a wireless communication interface of the medical implant 100. For example, the signaling may be communicated from the medical implant (through the wireless communication interface) to a clinician for analysis and determinations on possible treatments based on the signaled indications of electrical and/or chemical characteristics.

In some embodiments, the implant component 150 is electrically connected to the energy storage device 130 and is primarily or fully powered by the energy storage device 130.

Figure 1B:
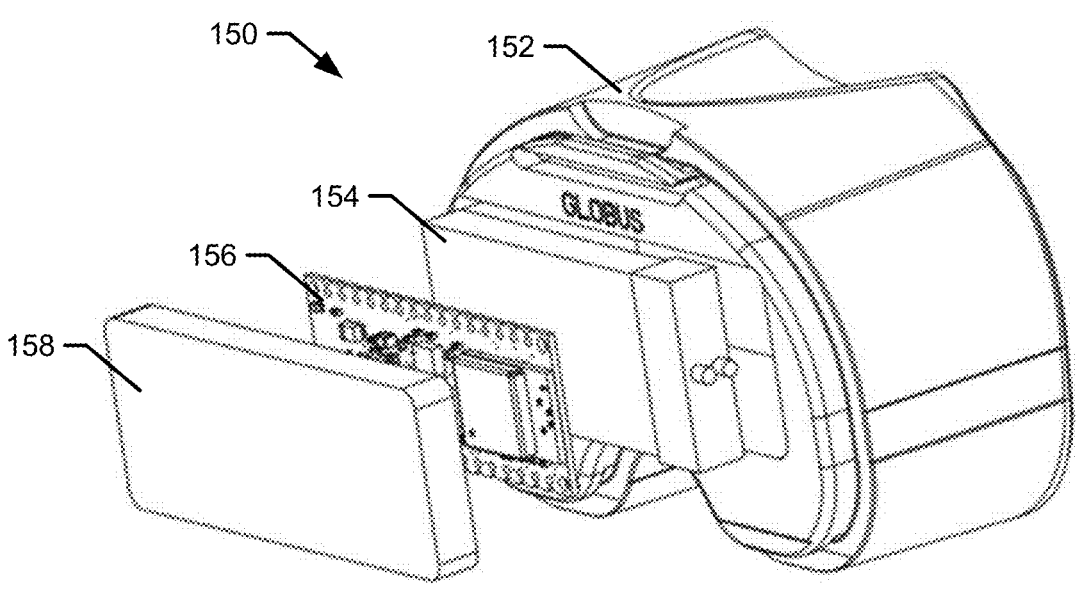
FIG. 1B illustrates an exploded isometric view of components of the implant component of the medical implant that is operative to supply voltage to at least one sensor electrode to measure electrical and/or chemical characteristics, according to some embodiments of the present disclosure.

FIG. 1B illustrates an exploded isometric view of components of the implant component of the medical implant that is operative to supply voltage to at least one sensor electrode to measure the electrical and/or chemical characteristics, according to some embodiments of the present disclosure.

Referring to FIG. 1B, the implant component 150 includes a support 152 that connects to (or forms part of) the tibial insert (e.g., tibial insert 110 of FIG. 1A) on which are mounted at least one electrode array comprising the at least two electrodes spaced apart on the implant component 150, an implant component energy storage device 154 (e.g., rechargeable battery or capacitive circuitry, that is additional to or alternative of the energy storage device 130), implant circuitry 156, and an enclosure 158 adapted to hermetically seal the implant circuitry 156 and implant component energy storage device 154 to the support 152 while implanted in the patient.

Figure 1C:
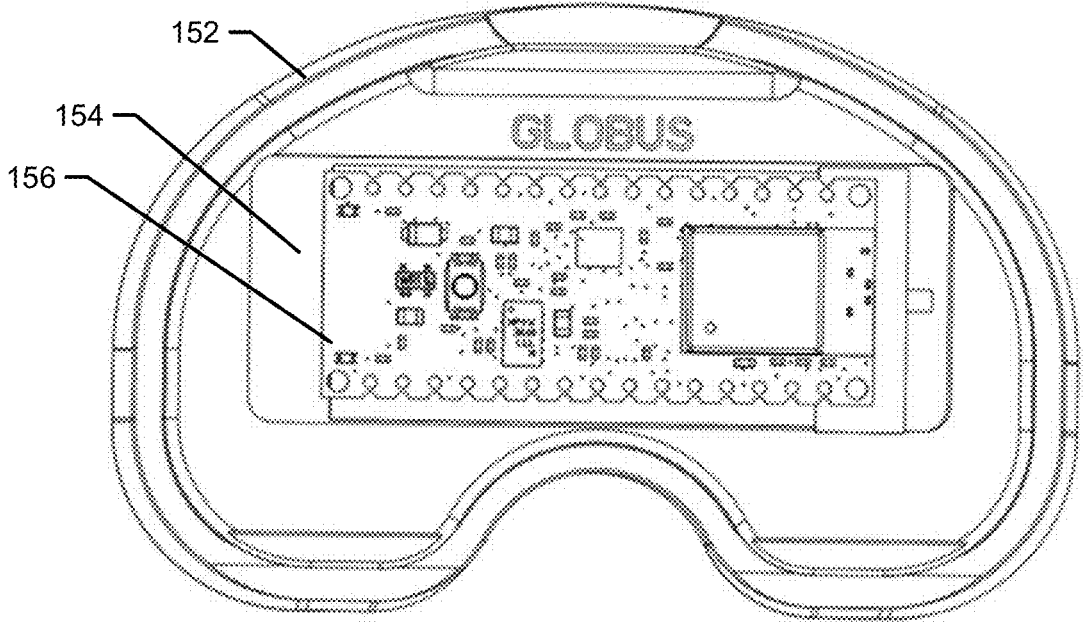
FIG. 1C illustrates a top view of the implant component of the tibial insert of FIG. 1B showing implant circuitry including a power management unit and a controller which are operative according to some embodiments of the present disclosure.

FIG. 1C illustrates a top view of the implant component of the tibial insert of FIG. 1B showing implant circuitry 156 which is operative to at least supply voltage (from implant component energy storage device 154 and/or energy storage device 130 of FIG. 1A) to at least one of the sensor electrodes to measure electrical and/or chemical characteristics, and communicate signaling based on the measured electrical and/or chemical characteristics through a wireless communication interface of the medical implant. In some embodiments, the implant circuitry 156 is powered primarily or fully by the energy storage device 130 of FIG. 1A. In embodiments where the energy storage device 130 is the primary source of power, the implant component energy storage device 154 acts as secondary or back-up power source.

Implant circuitry 156 may include one or more processor circuits ("processor") which execute instructions stored in one or more memory circuits ("memory").

In some embodiments, the electrodes in the electrode arrays 120 are electrically connected to the implant component 150 through insulated electrical traces or wires routed on the surface of the implant component 150 or through the body of the implant component 150. The electrical traces or wires may terminate at connectors that interface with pass-through connectors of the implant component 150. The housing (or support 152) of the implant component (along with other parts of the medical implant) may be constructed at least in part of a material that minimizes RF interference. In some embodiment, the top portions of the housing are constructed of a RF transparent material such as PEEK to allow transmission of the radio waves. In some embodiments, the bottom component of the housing could be constructed of an RF transparent material such as PEEK or an RF shielding material such as TAV (titanium).

In some embodiments, the implant circuitry is a printed circuit assembly (PCA). The PCA may include electronic components and circuitry required for communication, wireless charging, sensing, and stimulation, including the RF antenna(s).

Figure 2A:
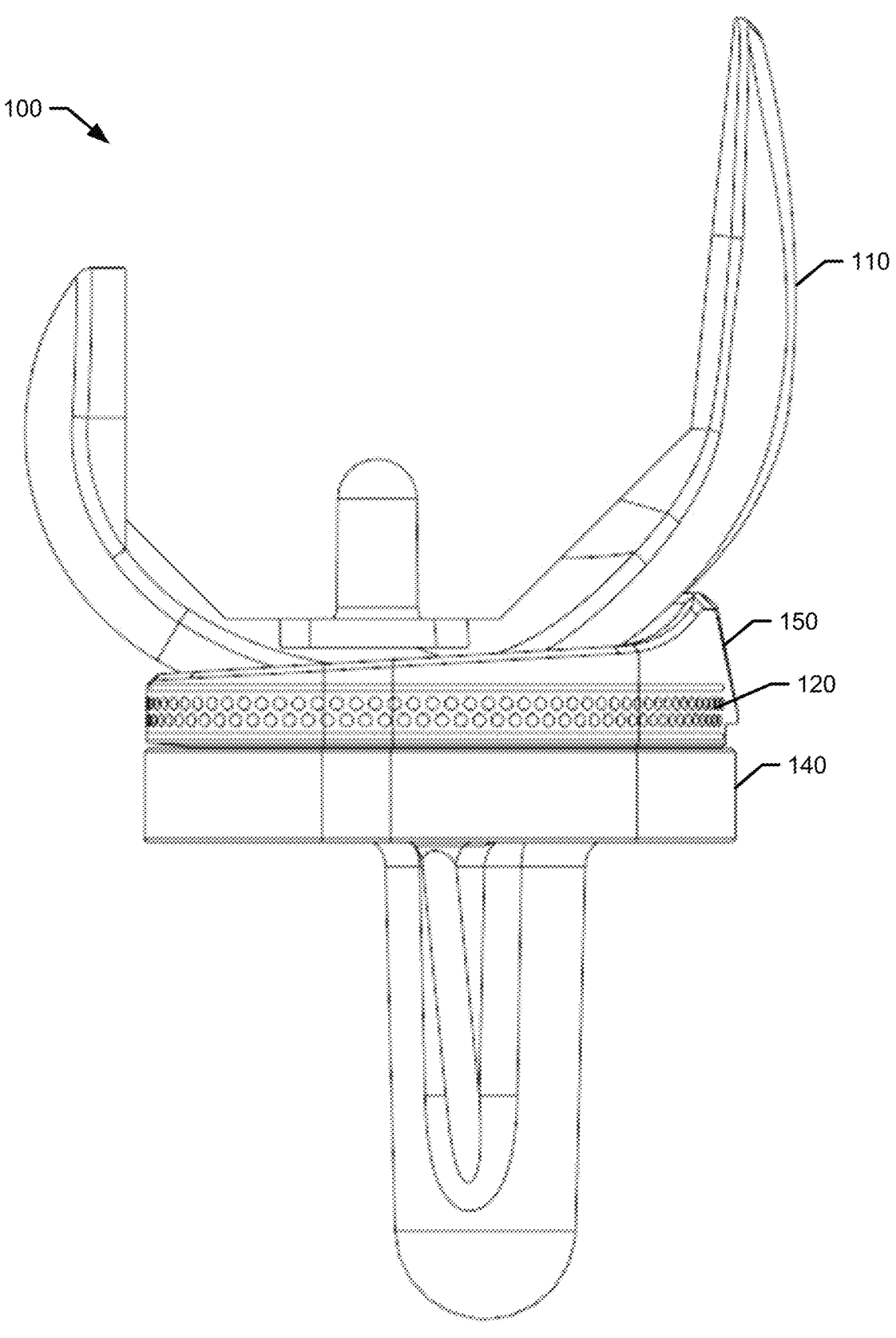
FIG. 2A illustrates a side view of the medical implant showing the tibial insert, implant component, and tibial tray physically connected, according to some embodiments of the present disclosure.

FIG. 2A illustrates a side view of medical implant 100 showing the tibial insert 110, implant component 150, and tibial tray 140 physically connected, according to some embodiments of the present disclosure. The implant component 150 includes a single electrode array 120 visible.

Figure 2B:
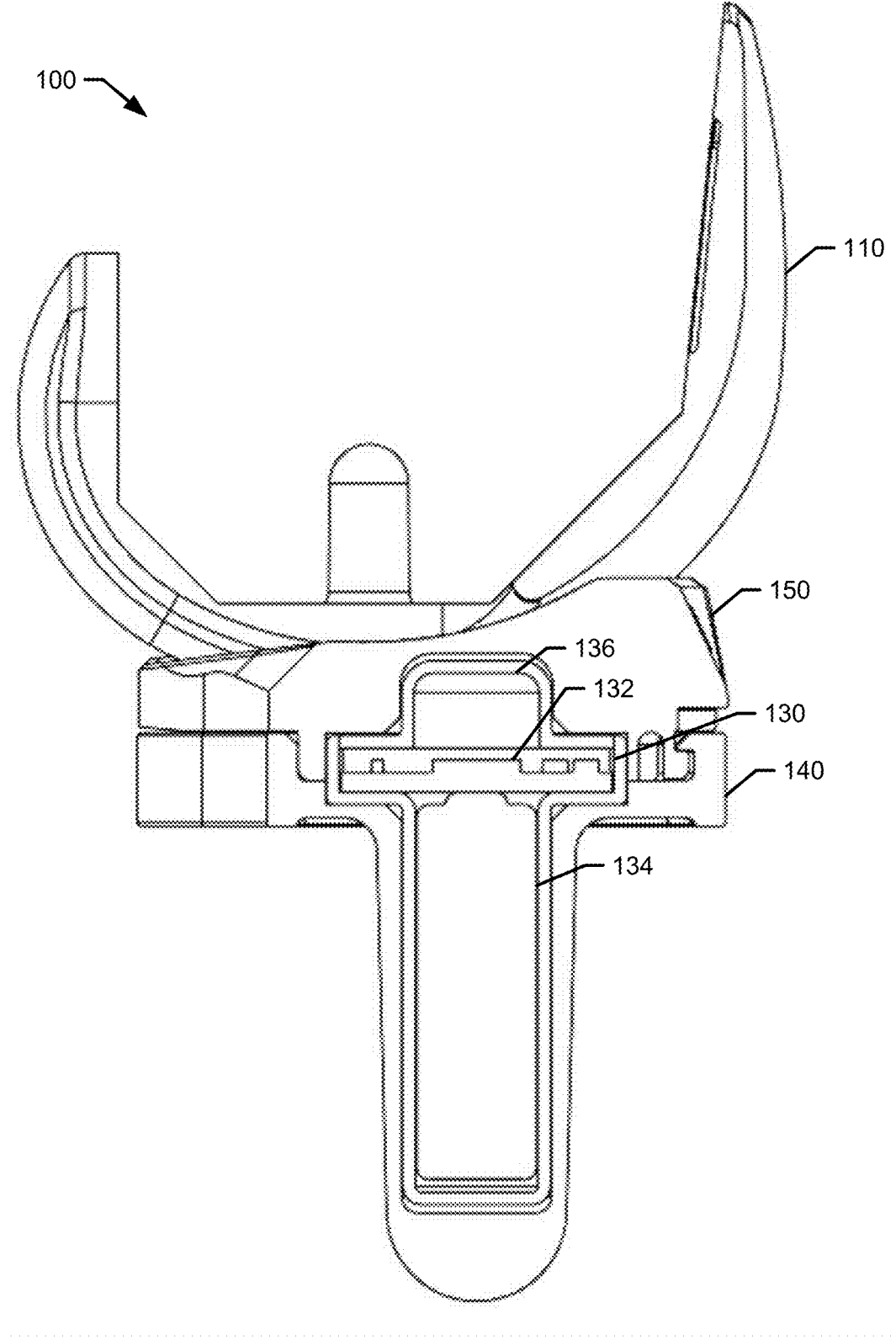
FIG. 2B illustrates the medical implant of FIG. 2A with the enclosures removed to expose an arrangement of the embedded energy storage device and electronics including a circuit board, a power management unit, controller, and sensors according to some embodiments of the present disclosure.

FIG. 2B illustrates the medical implant 100 of FIG. 2A with the enclosures removed to expose an arrangement of the embedded energy storage device 130 and electronics 132 including a circuit board, a power management unit, controller, and sensors according to some embodiments of the present disclosure. In some embodiments, the electronics 132 may perform the operations of the implant circuitry 156 or be in communication with the implant circuitry 156 to provide the power from a power resource 134 (e.g., rechargeable battery or capacitive circuitry) to other components of the medical implant (e.g., the electrode array(s)) through the component 136.

Figure 2C:
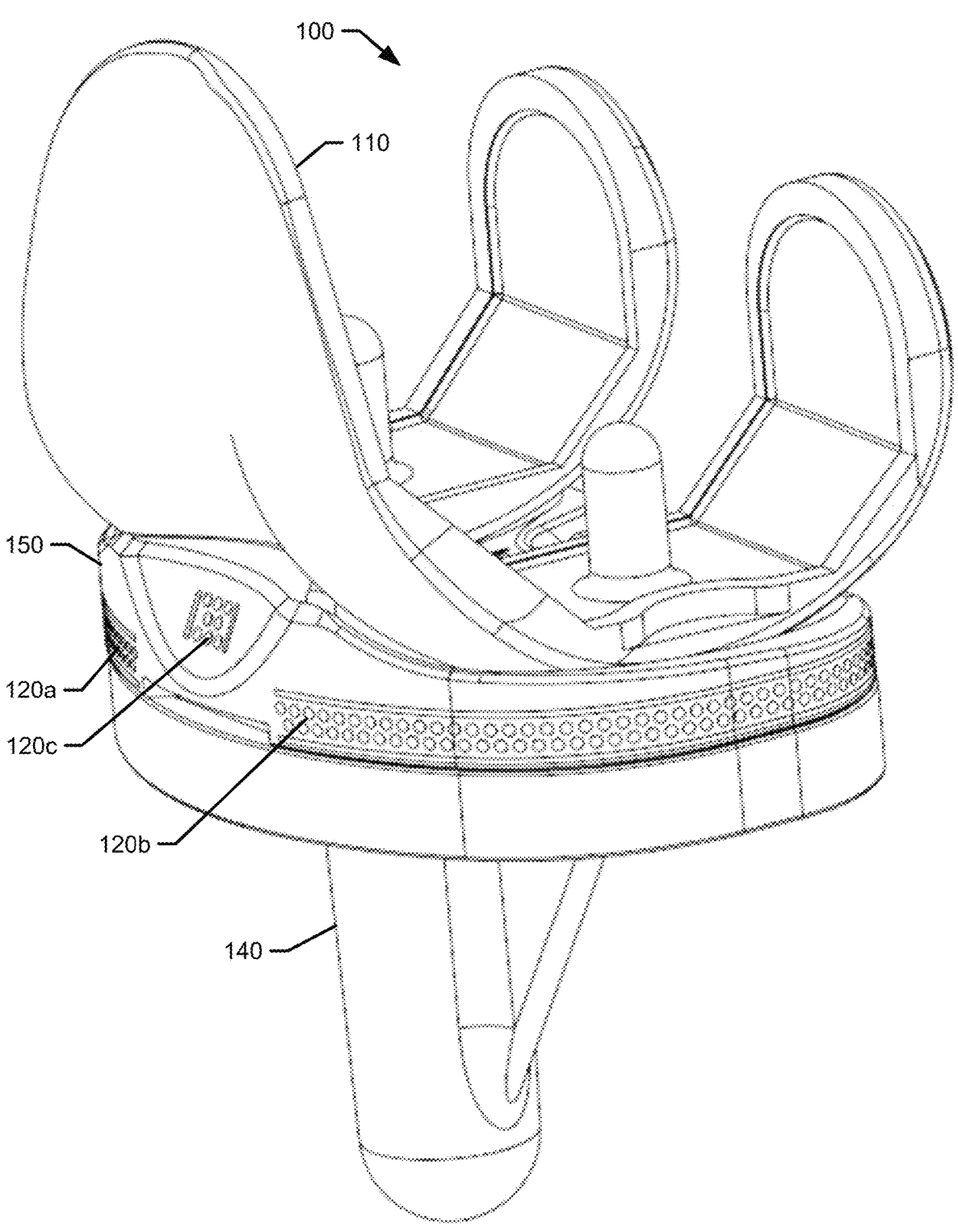
FIG. 2C illustrates another view of the medical implant with two electrode arrays on either side of the implant component and a third electrode array centrally located on a frontward face of the implant component, according to some embodiments of the present disclosure.

FIG. 2C illustrates another view of the medical implant 100 with two electrode arrays 120*a-b* along the side of the implant component 150 and a third electrode array 120*c* centrally located on a frontward face of the implant component, according to some embodiments of the present disclosure.

Figure 2D:
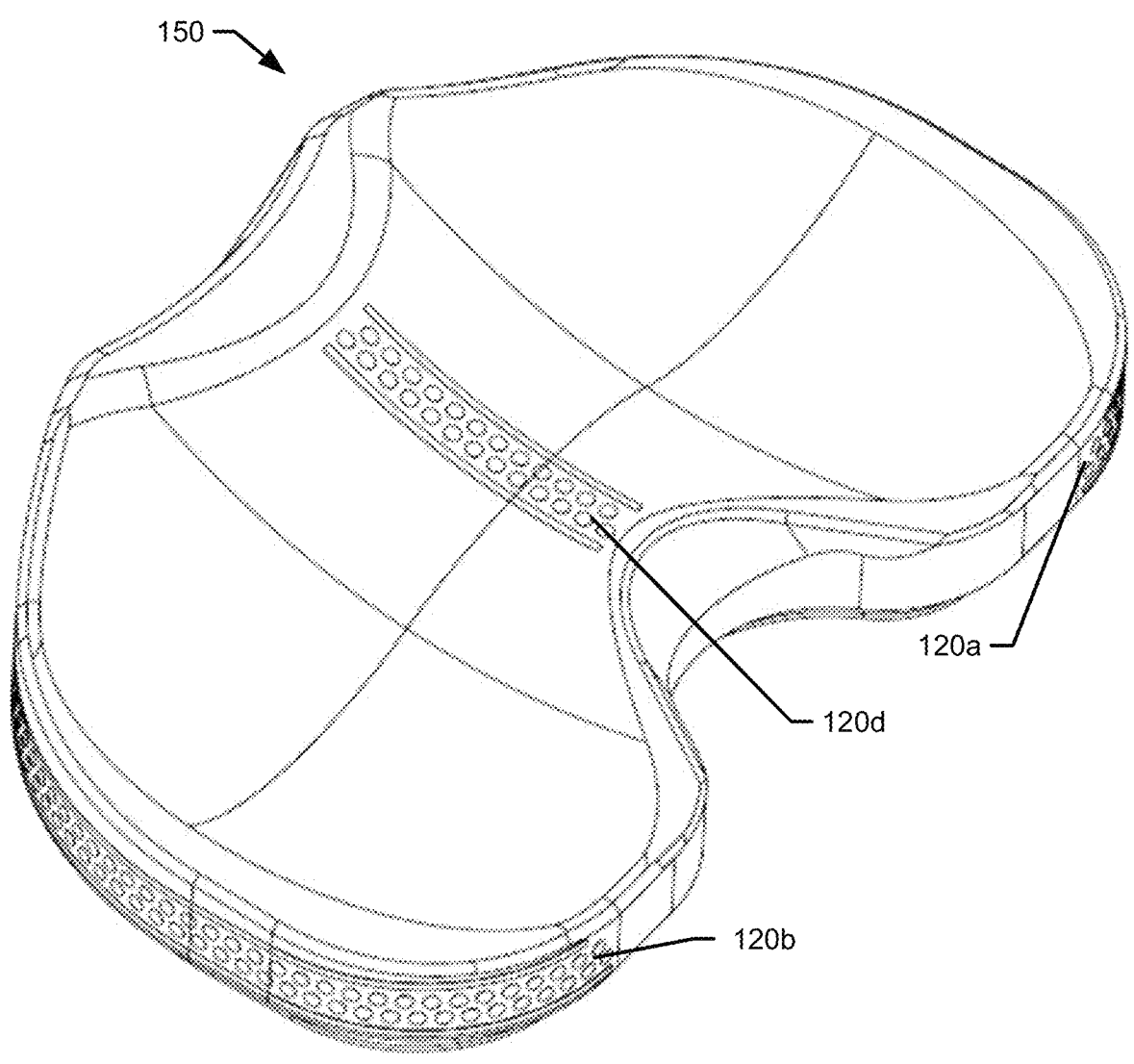
FIG. 2D illustrates the implant component with two electrode arrays on either side of the implant component and a third electrode array centrally located on a top of the implant component, according to some embodiments of the present disclosure.

FIG. 2D illustrates the implant component 150 with two electrode arrays 120*a-b* along the side of the implant component 150 and a third electrode array 120*d* centrally located on a top of the implant component 150, according to some embodiments of the present disclosure. In some embodiments, the third electrode array 120*d* is centrally located on top of the implant component 150 in order to not be in contact with the tibial insert 110 of FIG. 2C while the implant is in use by a patient.

Figure 2E:
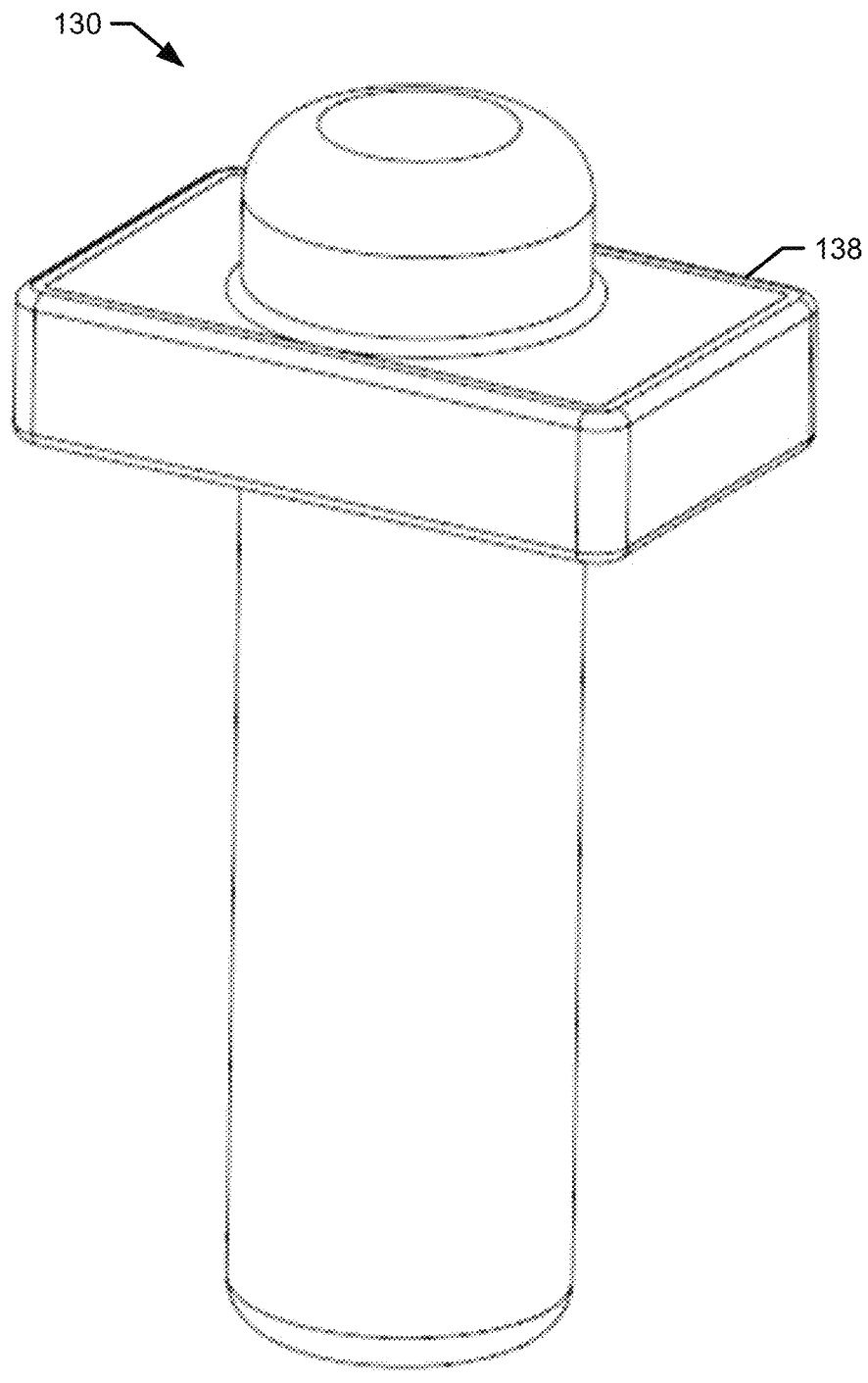
FIG. 2E illustrates the energy storage device of the medical implant, according to some embodiments of the present disclosure.

FIG. 2E illustrates the energy storage device 130 of the medical implant, according to some embodiments of the present disclosure. In some embodiments, the energy storage device 130 includes an enclosure 138 that hermetically seals the power resource, electronics, and component 136, but allows for power transfer from the power resource to other components of the medical implant.

Figure 2F:
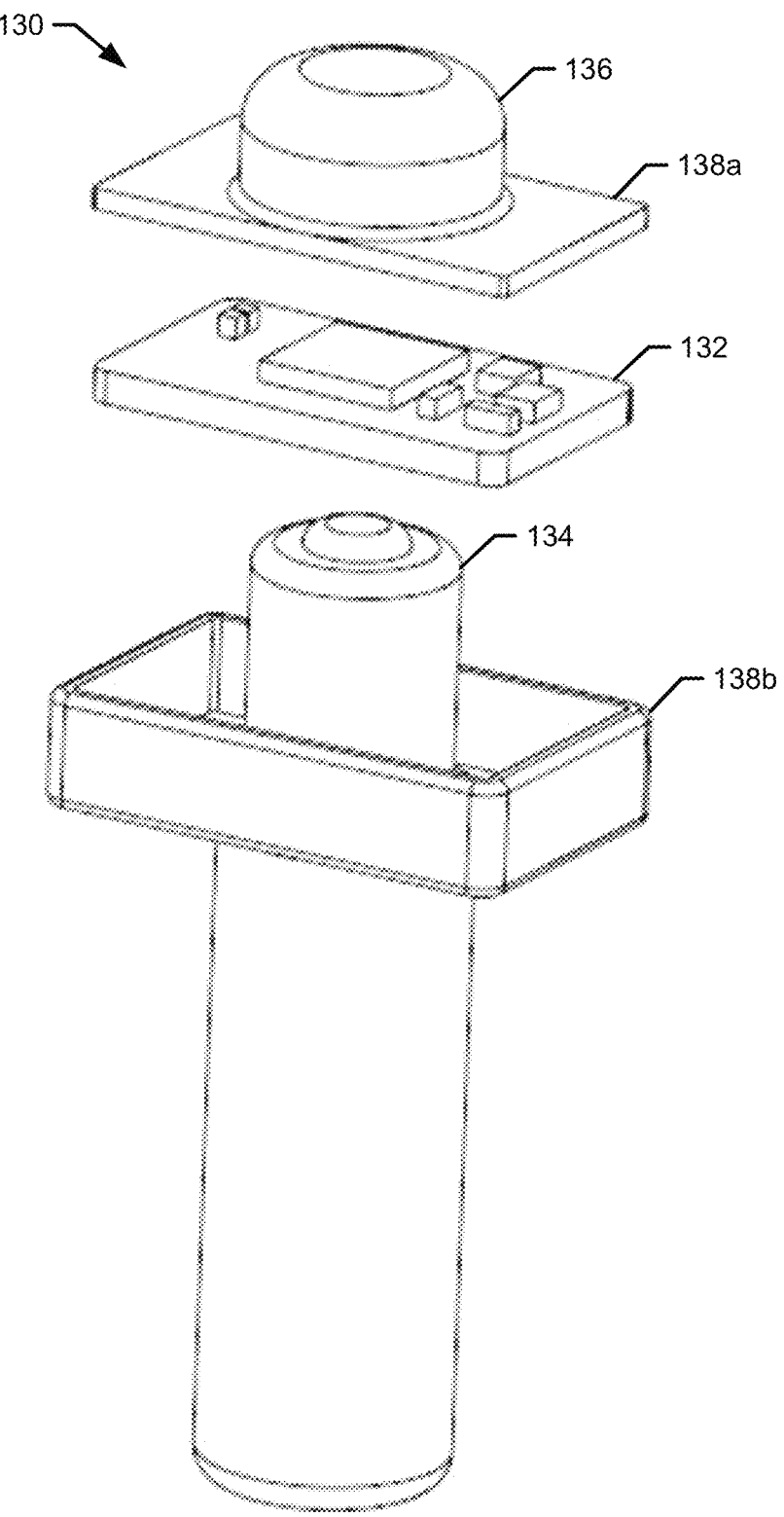
FIG. 2F illustrates an exploded isometric view of the energy storage device and electronics including a power management unit, controller, and sensors according to some embodiments of the present disclosure.

FIG. 2F illustrates an exploded isometric view of the energy storage device 130 and electronics 132 including a power management unit, controller, and sensors according to some embodiments of the present disclosure. In this view, the enclosure is separated apart such that enclosure 138*a* is detached from enclosure 138*b*.

Figure 3:
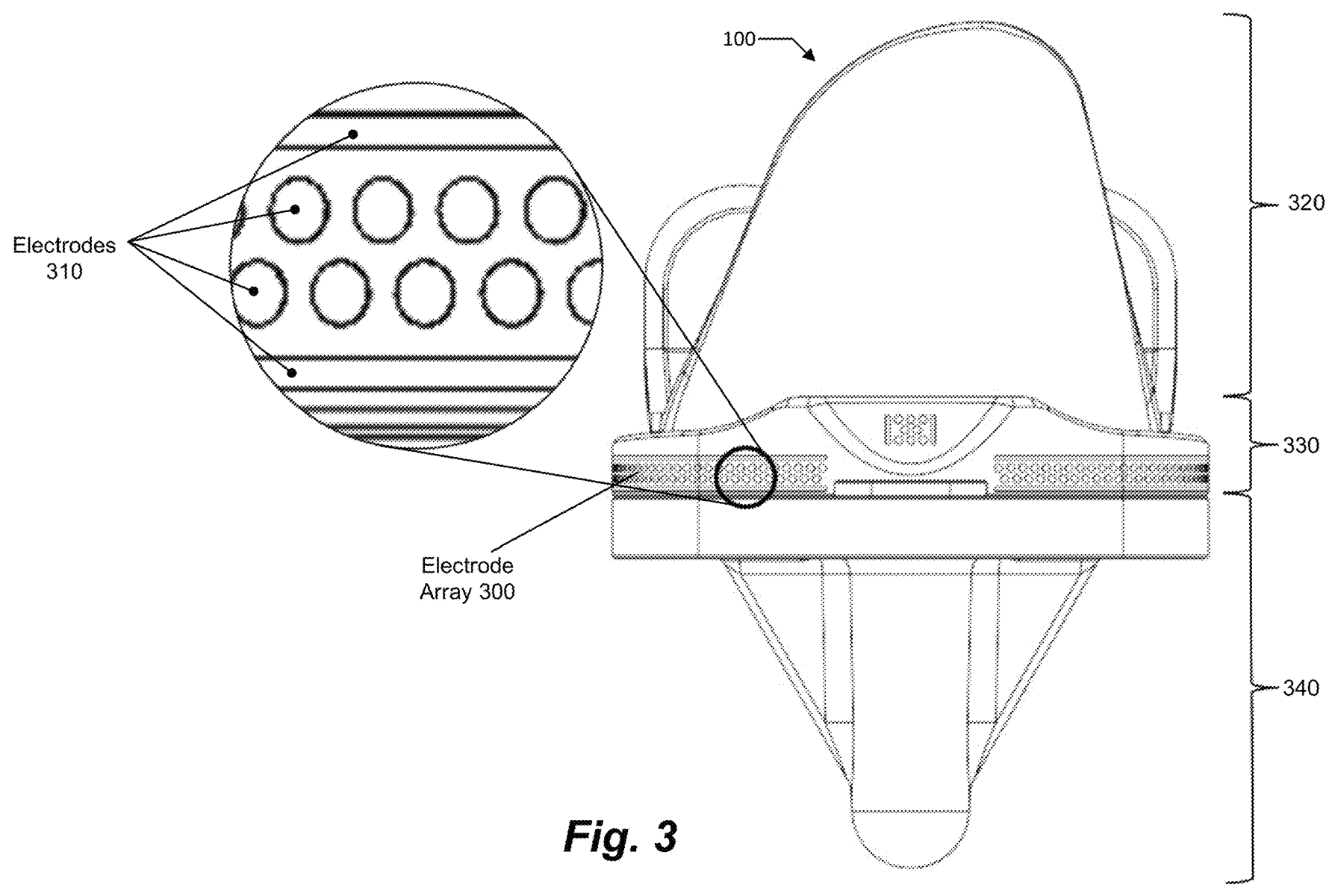

FIG. 3 illustrates a front view of medical implant 100 which includes a magnified view of one of the electrode arrays of the implant component, according to some embodiments of the present disclosure. The magnified view of electrode array 300 shows an arrangement of electrodes 310 spaced apart on the implant component. Additionally, portions of the medical implant are illustrated. Portion 320 illustrates the femoral component of the medical implant 100, portion 330 illustrates the tibial insert of the medical implant 100, and portion 340 illustrates the tibial tray of the medical implant 100.

Figure 4A:
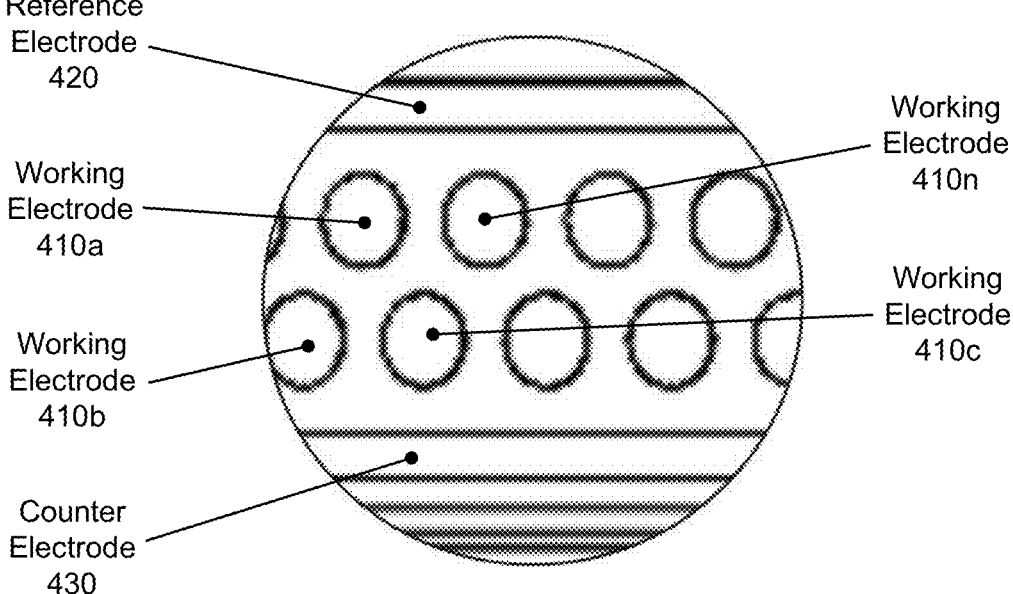
FIG. 4A illustrates a magnified view of the electrode array of the medical implant including a reference electrode, a plurality of working electrodes, and a counter electrode, according to some embodiments of the present disclosure.

FIG. 4A illustrates a magnified view of the electrode array of the medical implant including a reference electrode 420, a plurality of working electrodes 410*a-n*, and a counter electrode 430, according to some embodiments of the present disclosure.

In some embodiments of the present disclosure, the working electrodes 410*a-n* are sensor electrodes—capable of measuring and/or detecting electrical and/or chemical characteristics or a type of bacteria—and/or stimulation electrodes—capable of being electrically stimulated by current supplied by the energy storage device to be at a level which reduces the biofilm on at least part of the implant component while implanted in the patient.

The electrode material may include, but is not limited to, at least one of silver, silver chloride, gold, platinum, graphene, graphite, conducting polymers, or a combination thereof.

In some embodiments, the working electrodes of an electrode array are identical electrodes which are used for any combination of measuring electrical and/or chemical characteristics and electrical stimulation functions.

In some other embodiments, the working electrodes of an electrode array include an arrangement of specialized electrodes for various measuring of electrical and/or chemical characteristics and electrical stimulation functions.

In some embodiments, electrode arrays are included in 3-electrode systems with a reference electrode, working electrode, and counter electrode. In some embodiments, an upper linear electrode could function as the reference electrode (e.g., reference electrode 420), the middle circular electrodes could function as the working electrodes (e.g., working electrodes 410*a-n*), and the lower linear electrode could function as the counter electrode (e.g., counter electrode 430).

In some embodiments, the reference electrode 420 is an electrode that is supplied a fixed reference voltage (e.g., 1.7 volts) for the sensing measurements. For example, reference electrode 420 may provide a baseline against which the changes in potential at the working electrode(s) can be interpreted. By maintaining a stable and reproducible reference potential through the reference electrode, the electrode array may get more consistent electric signal response measurements so it is easier to analyze and interpret the electrical and/or chemical characteristics measured by the working electrodes.

In other embodiments, the reference electrode 420 is not used (or is not present) on the electrode array. In yet other embodiments, the reference electrode 420 is connected to the counter electrode thereby making them both act as counter electrodes. How the reference electrode is used may depend on the type of electrical and/or chemical characteristic that is being measured by the working electrode(s) or the measuring process used (e.g., amperometry).

The counter electrode 430 acts as the cathode in the three-electrode array system illustrated in these Figures.

The working electrode acts as the anode in the three electrode array system illustrated in these Figures, and is where the sensor measurements take place. For example, the working electrodes could be utilized for spatial mapping of a single parameter, such as impedance measurement, yielding an impedance measurement at each working electrode on the electrode array. Using multiple electrochemical techniques in series, such as potentiometry, electrochemical impedance spectrometry, and cyclic voltammetry, the array of working electrodes may also be used to capture multiple characteristic readings sequentially, such as impedance, conductivity, and pH. However, in some embodiments, different electrochemical techniques could be performed on individual working electrodes in parallel. For example, cyclic voltammetry could be performed on working electrode 410*a,* amperometry could be performed on working electrode 410*b,* and impedance spectroscopy could be performed on electrode 410*c*. The individual working electrodes could be grouped into a set of electrodes that are repeated to form an electrode array on the surface of the implant (discussed in more detail below).

Regarding the electrical stimulation of the working electrodes, the implant circuitry may be operative to control electrical stimulation of specific working electrodes, or all the working electrodes of an electrode array, by current supplied by the energy storage device to be at a level which at least reduces formation of a biofilm on at least part of the implant component while implanted in the patient. The implant circuitry may provide a voltage differential between a working electrode(s) and a counter electrode to cause electric field(s) to extend therebetween, and controls the level of current density therebetween to at least reduce formation of a biofilm and/or to at least partially eradicate a biofilm on at least part of the implant component while implanted in the patient. The counter electrode may be the counter electrode in the same electrode array or a counter electrode of a different electrode array than the one in which the working electrode(s) are being stimulated at. Alternatively, there may be a counter electrode that is not a part of an electrode array that is used while a working electrode(s) is stimulated.

Figure 4B:
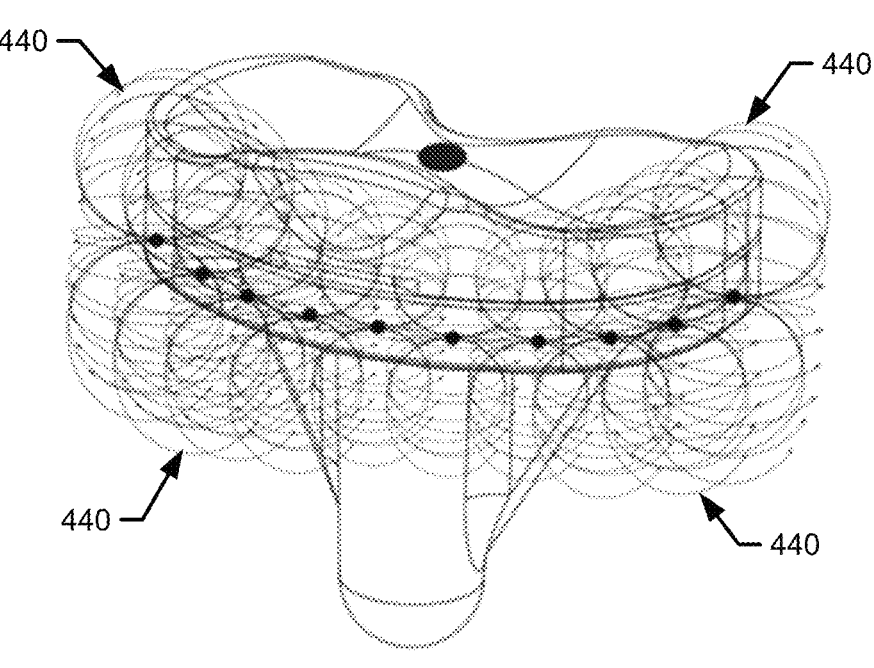
FIG. 4B illustrates electrical fields extending between the working electrodes and the counter electrode on the side surface while the electrode array of FIG. 4A is electrically stimulated, according to some embodiments of the present disclosure.

FIG. 4B illustrates electrical fields 440 extending between the working electrodes and the counter electrode on the side surface while the electrode array of FIG. 4A is electrically stimulated, according to some embodiments of the present disclosure.

Figure 4C:
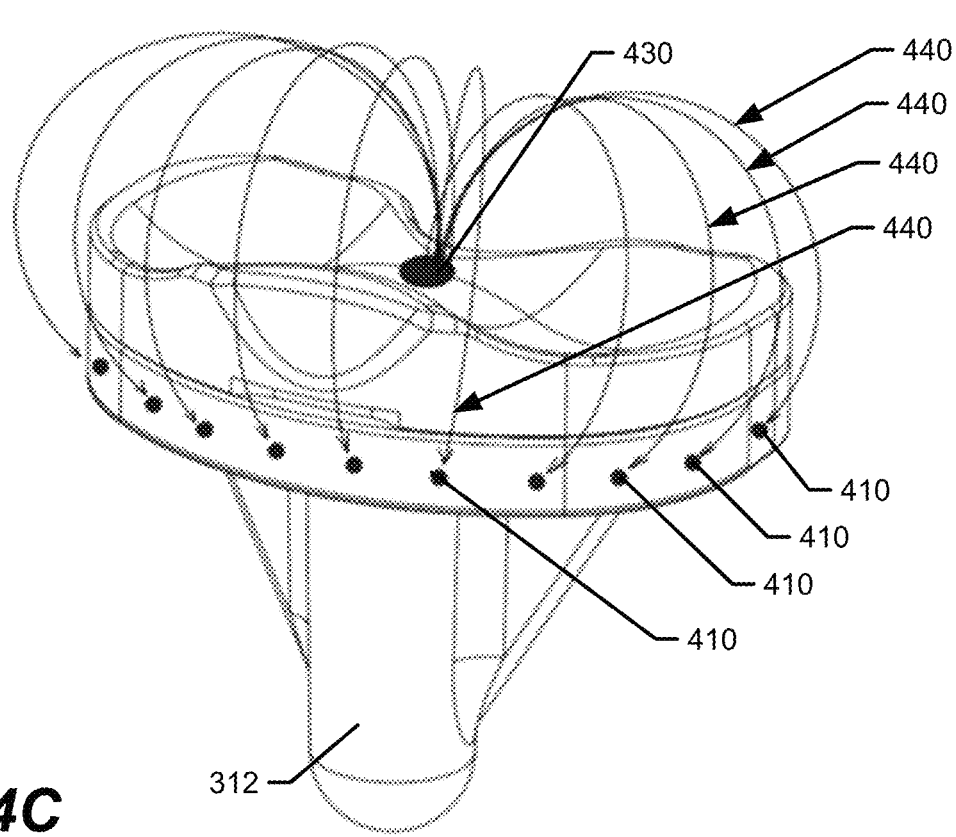
FIG. 4C illustrates electrical fields extending between the working electrodes on the side surface of the medical implant and a centrally located counter electrode on the implant component while the electrode array is electrically stimulated, according to some embodiments of the present disclosure.
Figure 5A:
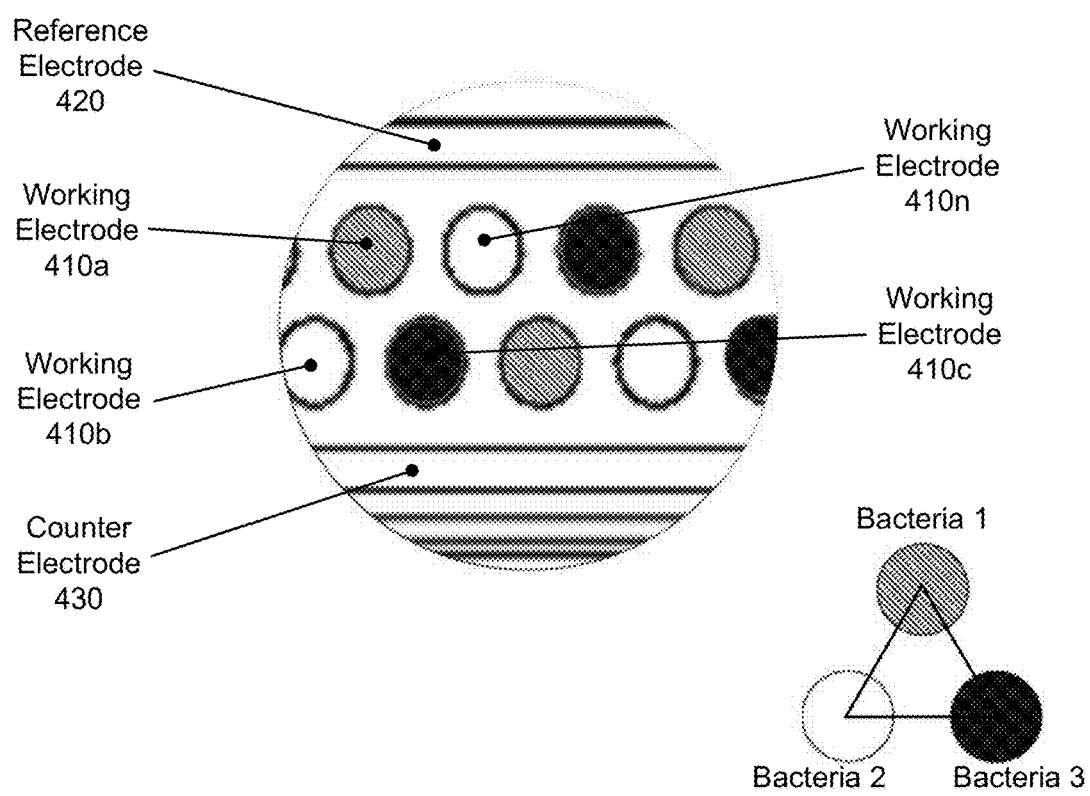
FIG. 5A illustrates another magnified view of the electrode array where the working electrodes are configured to measure or detect different types of bacteria, according to some embodiments of the present disclosure.

FIG. 4C illustrates electrical fields extending between the electrodes on the side surface and the centrally located electrode while the electrode array is electrically stimulated, according to some embodiments of the present disclosure FIG. 5A illustrates another magnified view of the electrode array where the working electrodes 410*a-n* are configured to measure or detect different types of bacteria or biofilm, according to some embodiments of the present disclosure. Some examples of types of bacteria that may be measured or detected by the working electrodes include, but are not limited to, Staphylococcus aureus, Staphylococcus epidermidis, and Streptococcus. For example, in FIG. 5A, the electrode array has sets of uniquely functionalized working electrodes. The working electrodes could be functionalized with antibodies to detect specific bacterial species. For example, the working electrode may have a functionalization layer on top of the electrode and then a bio-recognition element (e.g., enzyme, antibody, cell, and/or nucleic acid) on top the functionalization layer that allows the sensor electrode to detect or measure a specific electrical and/or chemical characteristic of the bacteria once it binds to the bio-recognition element on the working electrode.

In the example of FIG. 5A, the electrode array has sets of three working electrodes 410*a-c,* where each working electrode detects the presence of a unique bacterial species, such as *Staphylococcus aureus, Staphylococcus epidermidis*, and *Streptococcus*. While a set of three working electrodes is exemplified, it is noted that in some embodiments a set may include two or more working electrodes. In some embodiments, the different sets of working electrodes may overlap by at least one working electrode.

Additionally, in some embodiments, the working electrodes 410*a-n* may be configured to detect more than one type of bacteria or biofilm.

Figure 5B:
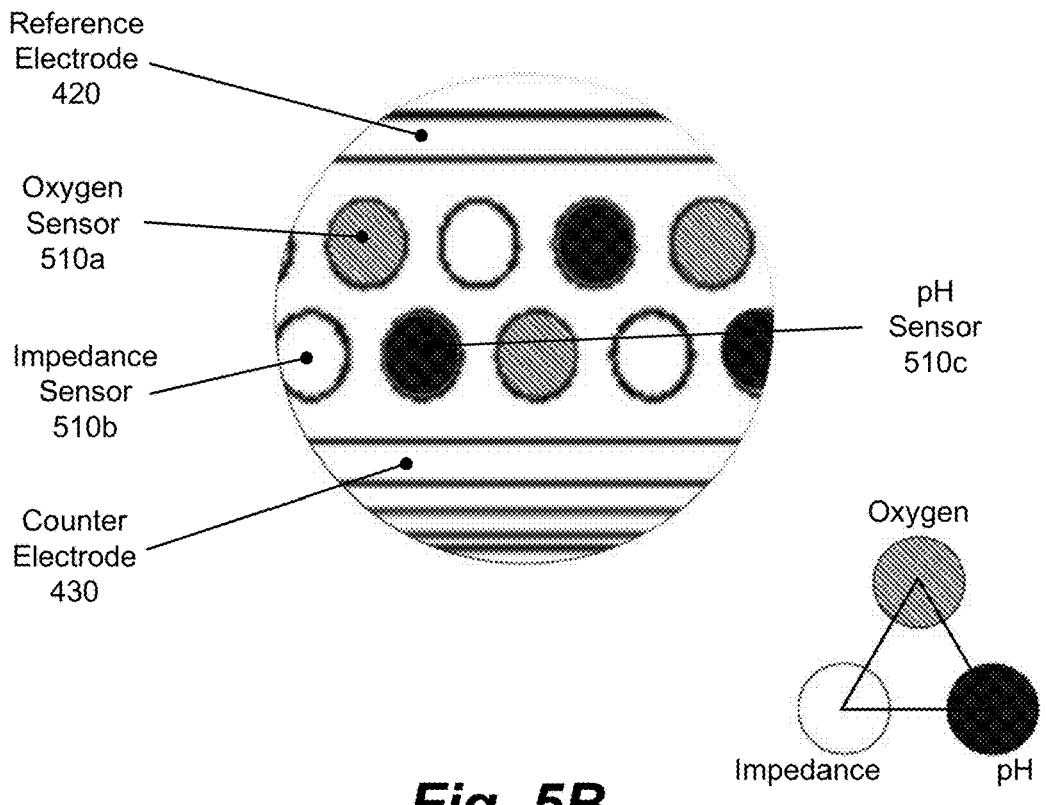
FIG. 5B illustrates yet another magnified view of the electrode array where each working electrodes is configured as an oxygen sensor, impedance sensor, or a potential hydrogen (pH) sensor, according to some embodiments of the present disclosure.

FIG. 5B illustrates yet another magnified view of the electrode array where each working electrode is configured as an oxygen sensor, impedance sensor, or a potential hydrogen (pH) sensor, according to some embodiments of the present disclosure. In this embodiment, the electrode array has sets of uniquely functionalized working electrodes to determine specific electrical and/or chemical characteristics which are correlative with the formation of bacterial biofilm. For example, each set can include an oxygen sensor 510*a*, impedance sensor 510*b*, and pH sensor 510*c*.

Additionally, in some embodiments, the working electrodes 510*a-c* may be configured to measure more than one type of electrical and/or chemical characteristic.

In some embodiments, the electrode array has any combination of working electrodes where at least one working electrode (or set of working electrodes) is configured to measure electrical and/or chemical characteristics and another at least one working electrode (or another set of working electrodes) is configured to detect a type of bacteria or biofilm.

When no biofilm is present, the average readings/measurements of each sensor electrode type across the electrode array may provide a characterization of the macro environment, namely the synovial fluid that surrounds the prosthetic joint. While certain parameters/characteristics, such as dissolved oxygen and impedance may not always have direct clinical relevance, the synovial fluid pH may be helpful in providing the clinician knowledge of the healing process and development of complications. For example, the synovial fluid pH from patients with periprosthetic joint infections typically ranges lower than normal, between 6 and 7.2. Normal pH is typically considered between 7.3 and 7.8.

Biofilm typically forms non-uniformly in one or more spots on the surface of the implant where planktonic bacterial attachment is preferential due to surface roughness or other factors. In some embodiments, the working electrodes could be intentionally designed to serve as the preferential attachment surface for planktonic bacteria, thereby increasing the probability that a bacterial biofilm forms on the sensor array rather than a non-instrumented portion of the implant surface. For example, the working electrodes and/or the surfaces surrounding the working electrodes may be configured to have a rougher surface than the rest of the medical implant in order to create a more preferential attachments surface for the bacteria to form than the rest of the medical implant.

Figure 6:
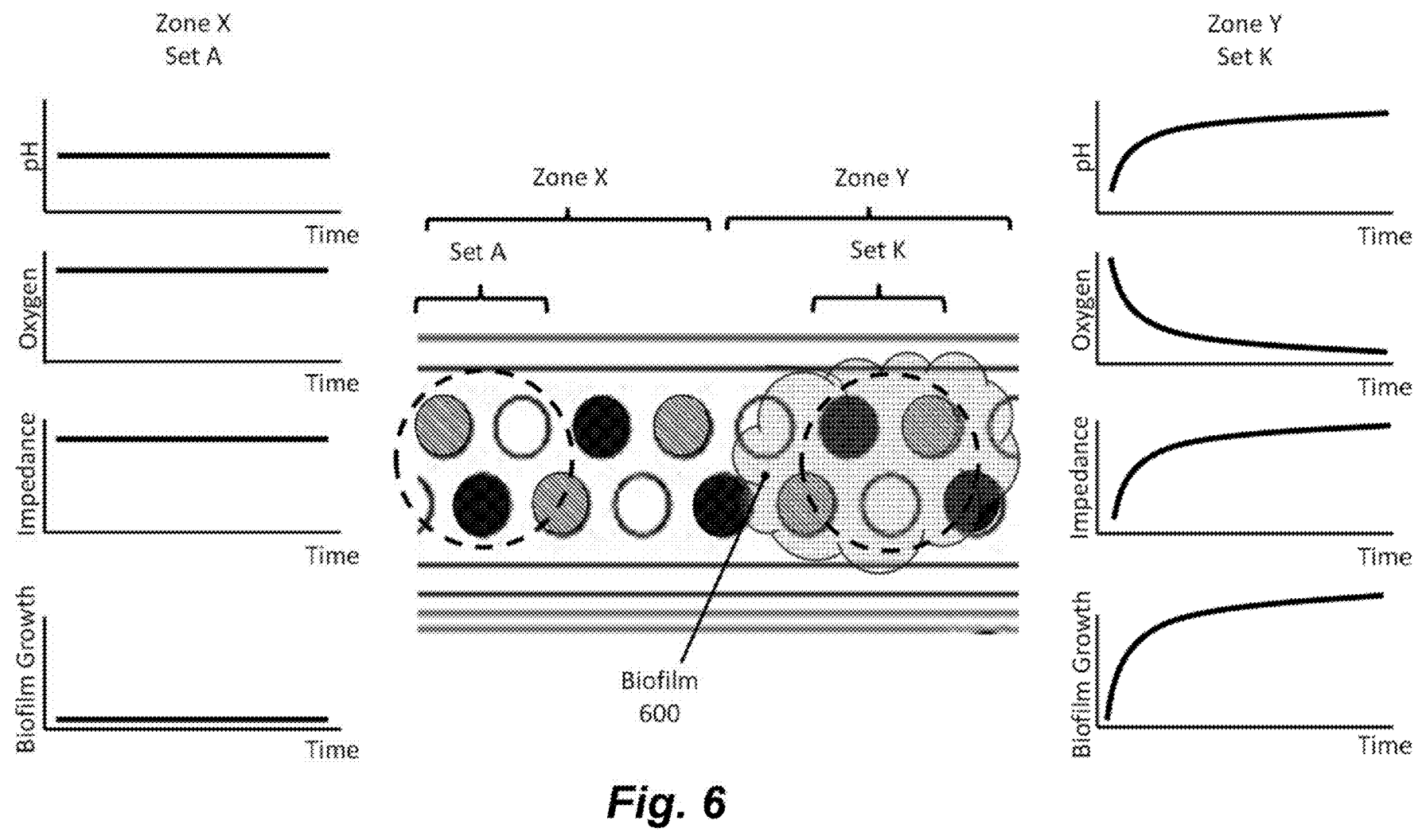

FIG. 6 illustrates a view of the electrode array with biofilm built up on the electrode array, and the electrode array is divided into sets and zones of electrodes, according to some embodiments of the present disclosure.

Referring to FIG. 6, if a biofilm forms on one or more electrodes (or set(s) of electrodes, for example Set K), the measurements of electrical and/or chemical characteristics from those electrodes could indicate the presence of biofilm as well as characterization of the biofilm growth state. For example, calibration curves, correlations, and/or machine learning models could be developed using in vitro and in vivo testing to relate the readings of electrochemical sensors with the presence and amount of biofilm on those sensors. For one such bacterial biofilm, the measured pH and impedance might increase while the oxygen decreases with the increase in biofilm growth. The combination of more than one type of sensor may allow for more robust and reliable correlations with biofilm growth.

By comparing localized readings from one or more sets of sensors with other sets of sensors or the average of all sensor readings, the the implant component (e.g., implant component 150) or a computing device (discussed in more detail below) can indicate the specific location of biofilm growth on the implant surface. For example, multiple sets of sensor electrodes may be arranged in zones (e.g., Zone X and Zone Y) around the medical implant. The sensor electrodes in Set A within Zone X measure the electrical and/or chemical characteristics of the synovial fluid that contacts these sensor electrodes directly due to the lack of biofilm in growth in this area. Other sets within Zone X should provide readings/measurements that are consistent with Set A since all the sensor electrodes in the zone are in contact with the same synovial fluid, with no biofilm present. If the sensor electrodes in Set K within Zone Y are in contact with a bacterial biofilm, the sensor electrodes will yield readings/measurements that are indicative of biofilm formation. The readings/measurements of Set K could then be compared to the readings of Set A to indicate that a biofilm is present specifically in Zone Y, which maps to a specific location of the implant surface. This localized biofilm detection information could then be used to inform the clinician of the specific location of the biofilm growth. This information could then be utilized to perform targeted electrical stimulation to help remove or eradicate the biofilm altogether. After the stimulation treatment is administered, the measurement from the sensor electrodes in Set K may match readings to Set A and all other sets, indicating that the biofilm is removed and only the synovial fluid is in contact with the electrode array.

Figure 7:
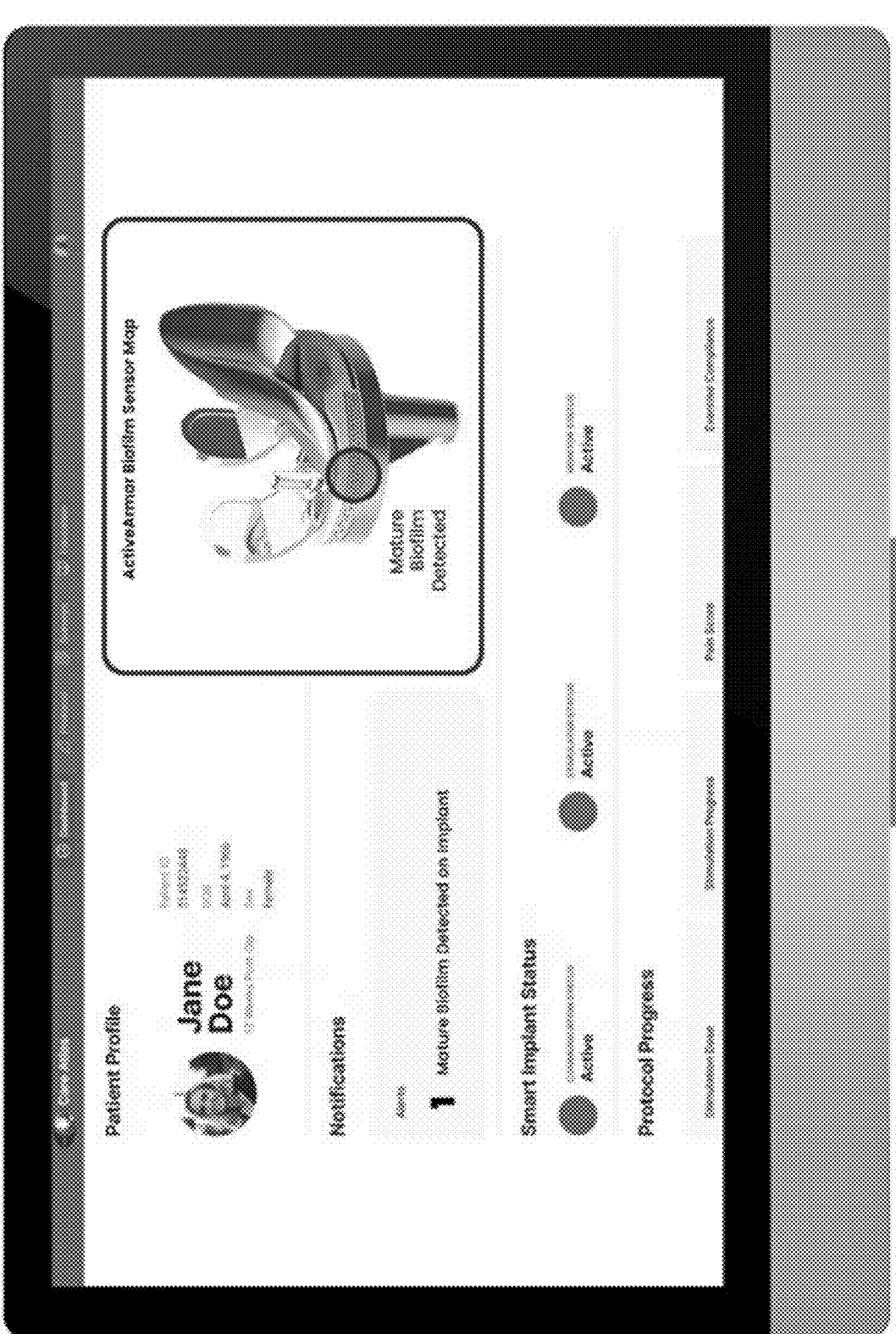
FIG. 7 illustrates an example clinician dashboard that depicts information received from the medical implant, according to some embodiments of the present disclosure.

FIG. 7 illustrates an example clinician dashboard that depicts information received from the medical implant, according to some embodiments of the present disclosure. In this example, the medical implant may communicate signaling indicating the electrical and/or chemical characteristics, that was measured by sensor electrodes of the medical implant, through the wireless communication interface to the computing device. The computing device is a device which is remotely located outside the body of the patient to receive signaling such as a smart phone, laptop or a desktop computer located nearby. The signaling may also indicate at least one of patient information that identifies the patient, a location of the sensor electrodes (or electrode arrays) from where the electrical and/or chemical characteristics were measured, whether biofilm is detected, a battery level of the energy storage device within the medical implant, and or other information relating to an operation or function of the medical implant.

The computing device may then process the received signaling and display a clinician dashboard similar to the clinician dashboard shown in FIG. 7, to allow the clinician to observe the computing device received signaling.

Figure 8:
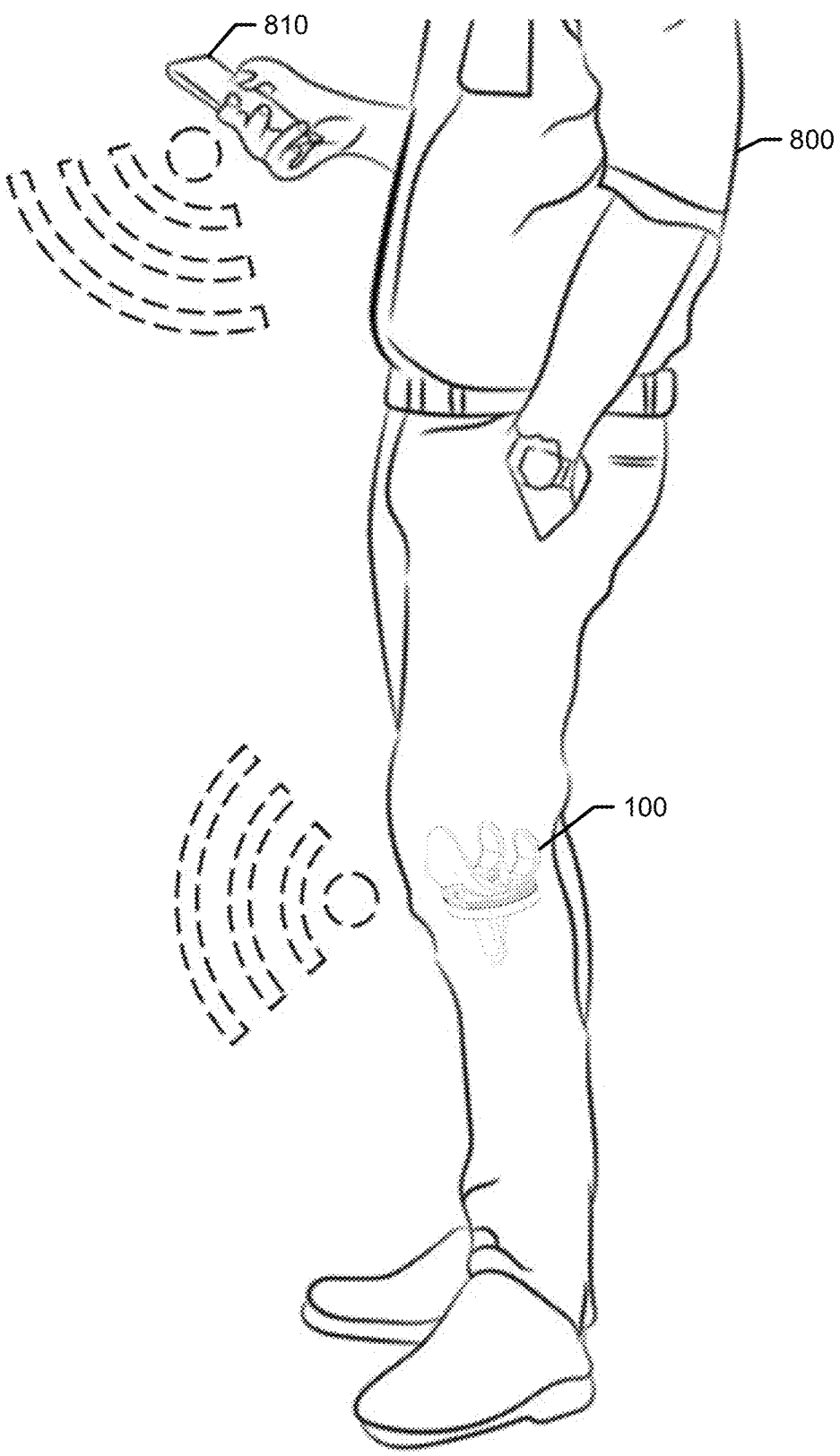
FIG. 8 illustrates a patient with the medical implant that is implanted in the patient and is configured to communication signaling to a mobile device of the patient, according to some embodiments of the present disclosure.

FIG. 8 illustrates a patient 800 with the medical implant 100 that is implanted in the patient 800 and is configured to communication signaling to a mobile device 810 of the patient 800, according to some embodiments of the present disclosure. The mobile device 810 may be a smart phone, computer, tablet, etc.

Figure 9:
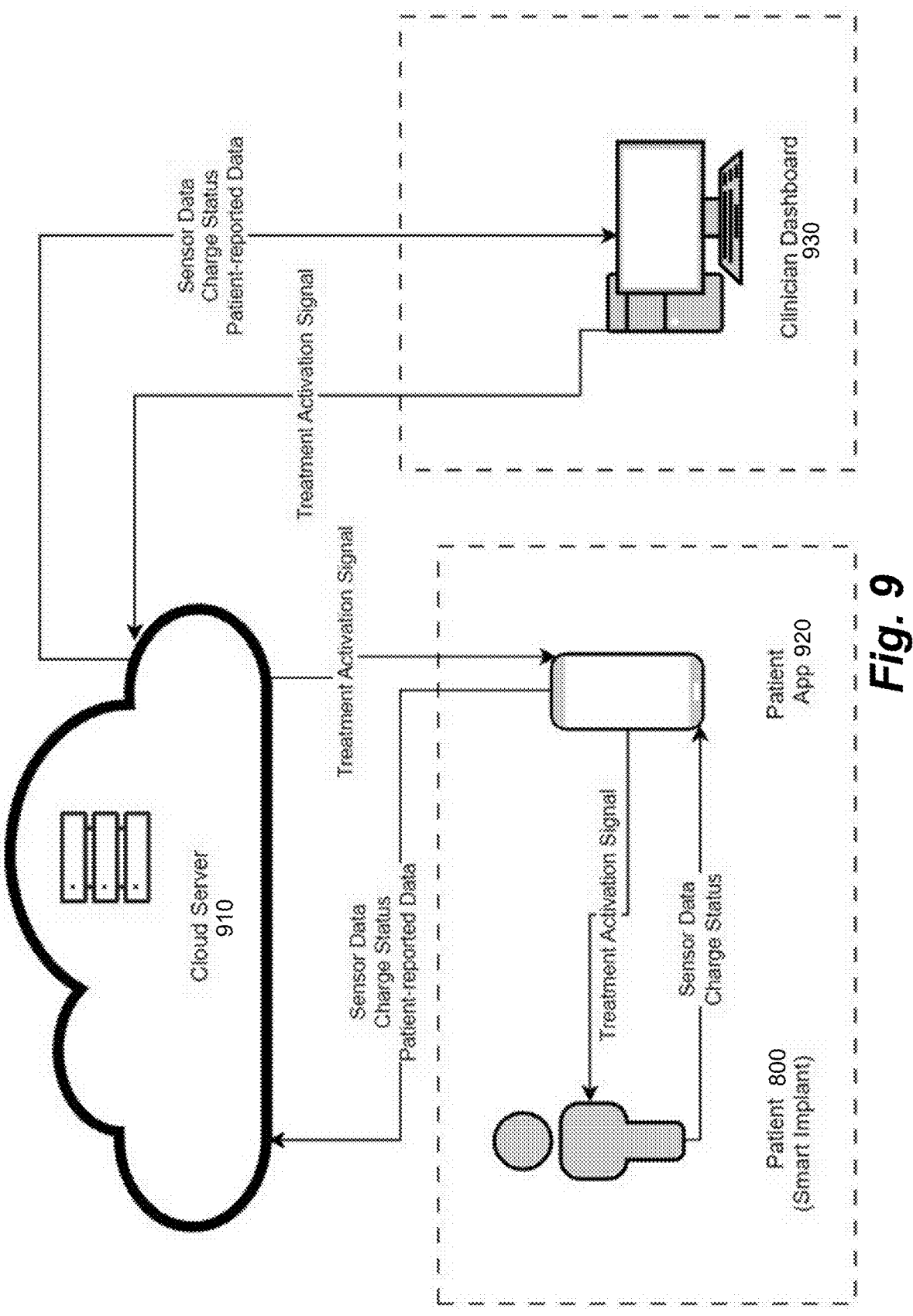
FIG. 9 illustrates a system that includes a cloud server, patient application, and clinician dashboard, according to some embodiments of the present disclosure.

FIG. 9 illustrates a system that includes a cloud server 810, patient application (also referred to as patient app) 920, and clinician dashboard 930, according to some embodiments of the present disclosure.

FIG. 9 shows the system of the present disclosure where in some embodiments, post-operatively, the medical implant senses the presence of bacterial biofilm on the surface of the medical implant components and transmits the sensor electrode readings to the clinician. The clinician decides on treatment based on sensor readings, information provided to the clinician through the accompanying patient app 920, and direct consultation. If the clinician determines that the patient has developed or is likely to develop an infection, the clinician can remotely activate a biofilm eradication program (electrical stimulation of the electrodes) on the patient's medical implant. The medical implant treatment may or may not be administered in combination with an antibiotic regimen. In addition, the clinician may also activate (through transmission from the computing device to the medical implant) a biofilm prevention program to prevent the formation of biofilm in the post-op recovery period of the index orthopedic procedure or following subsequent high-risk events such as dental procedures or urinary tract infections.

Referring to FIGS. 8 and 9, in some embodiments, the medical implant (e.g., medical implant 100) in patient 800 includes an implant component (e.g., implant component 150) configured to be implanted in patient 800. The medical implant may further include an electrode array (e.g., one of electrode arrays 120) comprising sensor electrodes spaced apart on the implant component. The medical implant may further include an energy storage device (e.g., energy storage device 130) inside the implant component and a wireless communication interface inside the implant component, configured to communicate with a wireless receiver that is separate from the medical implant. Additionally, the medical implant may include an implant circuitry (e.g., implant circuitry 156) inside the implant component and operative to supply voltage to at least one of the sensor electrodes to measure electrical and/or chemical characteristics and communicate signaling indicating the electrical and/or chemical characteristics through the wireless communication interface.

For example, the smart implant communicates with the patient's mobile phone 810, through the wireless communication interface, over a 2.4 GHz protocol such as Bluetooth® or Bluetooth® Low Energy (BLE). A mobile device compatible dongle may also be used to communicate to the wireless communication interface of the medical implant 100 on a radio frequency (RF) band that is not directly supported by the mobile device 810, such as 915 MHz or 401-406 MHZ (MICS). The mobile device compatible dongle would contain transmission and receiver antenna(s) tuned to the target frequency of the medical implant communication protocol. In either scenario, the signaling is sent from patient's medical implant 100, received by the mobile device's integrated antenna or dongle's antenna, and then processed through a dedicated patient app 920 on the patient's mobile device 810.

In some embodiments, the electrical and/or chemical characteristics indicate at least one of impedance, conductivity, and potential hydrogen (pH).

In some embodiments, the implant circuitry is further operative to supply a defined range of frequencies, or a specific frequency, to the sensor electrodes to measure electrical and/or chemical characteristics. This may provide the benefit of measuring a range of frequencies in order to detect or measure a type of bacteria or biofilm that has a predetermined resonant/exultation frequency. Thus, the defined range of frequencies is adapted to electrically excite one or more types of bacterial species (targeted species that are particularly dangerous for PJI.

In some embodiments, one or more of the sensor electrodes is configured to detect presence of a type of bacterial species. In these embodiments, one or more sensor electrodes is coated with a bio-recognition element adapted to bind to the type of bacterial species.

In some embodiments, the electrode array includes a first zone (e.g., zone X of FIG. 6) of at least one sensor electrode of the sensor electrodes and a second zone (e.g., zone Y of FIG. 6) of at least one electrode of the sensor electrodes, wherein the first zone and second zone are separate. In these embodiments, the implant circuitry is further operative to compare the electrical and/or chemical characteristics from the at least one sensor electrode in the first zone to the electrical and/or chemical characteristics of the second zone, and generate the signaling to indicate the presence of a biofilm and/or indicate the electrical and/or chemical characteristics from the at least one sensor electrodes in the first zone and second zone, based on the electrical and/or chemical characteristics from the at least one sensor electrode in the first zone being a threshold difference from the electrical and/or chemical characteristics from the at least one sensor electrode in the second zone.

In some embodiments, the sensor electrodes include at least one of an oxygen sensor, impedance sensor, and a pH sensor.

In some embodiments, the signaling may further indicate a charge status of the medical implant. For example, the indication of the charge status may be a batter level of the energy storage device (e.g., energy storage device 130) or the implant component energy storage device (e.g., implant component energy storage device 154).

In some embodiments, the electrode array further includes stimulation electrodes spaced apart on the implant component, and the implant circuitry is further operative to electrically stimulate at least one of the stimulation electrodes by current supplied by the energy storage device to be at a level which reduces a biofilm on at least part of the implant component while implanted in the patient. The implant circuitry may control the current supplied by the energy storage device to the stimulation electrodes to be a level sufficient to form hydrogen bubbles through reaction with patient fluid and dislodge the biofilm and/or to change potential hydrogen (pH) of the patient fluid to a level which reduces the biofilm.

Additionally or alternatively, in some embodiments, the implant circuitry is further operative to simultaneously measure the electrical and/or chemical characteristics through the sensor electrodes and to electrically stimulate the stimulation electrodes. Additionally or alternatively, in some embodiments, the implant circuitry is further operative to increase or decrease the current supplied by the energy storage device to the stimulation electrodes responsive to the electrical and/or chemical characteristics.

By simultaneously measuring electrical and/or chemical characteristics through the sensor electrodes and electrically stimulating the stimulation electrodes, the electrical and/or chemical characteristics may be used as a feedback loop for determining if the biofilm has been reduced, removed from the medical implant or eliminated. Additionally, the electrical and/or chemical characteristics may be used as a feedback loop for determining if higher or lower current should be supplied to the stimulation electrodes, for example, to help increase the likelihood of removing or eliminating the biofilm. For example, the feedback loop may provide closed-loop control of current level used for stimulation so as to provide a highest current level within a defined range through selected stimulation electrode(s) to be used for removing a biofilm while monitoring sensor feedback from selected sensor electrode(s) to ensure pH remains in an acceptable range.

In some embodiments, the implant circuitry is further operative to determine presence of a biofilm based on the electrical and/or chemical characteristics, and generate the signaling to indicate the presence of the biofilm and/or indicate the electrical and/or chemical characteristics, based on the determined presence of the biofilm. Additionally or alternatively, in some embodiments, the implant circuitry is further operative to generate the signaling to further indicate locations on the implant component that correspond to where the electrical and/or chemical characteristics indicate the presence of the biofilm. Additionally or alternatively, in some embodiments, the electrode array further includes stimulation electrodes spaced apart on the implant component and the implant circuitry is further operative to electrically stimulate at least one of the stimulation electrodes on a part of the implant component associated with the biofilm by current supplied by the energy storage device to be at a level which reduces the biofilm.

In some embodiments, the electrode array further includes stimulation electrodes spaced apart on the implant component, and the implant circuitry is further operative to detect presence of the biofilm and/or a type of bacteria and a location of the biofilm and/or the type of bacteria based on the electrical and/or chemical characteristics, and stimulate the stimulation electrodes in the location based on the detected presence of the biofilm and/or the type of bacteria. The implant circuitry may be further operative to control the duration and/or level of stimulation of the stimulation electrodes based on the detected type of bacteria.

In some embodiments, the implant circuitry further includes a memory and is further operative to save the electrical and/or chemical characteristics to the memory and to generate the signaling to indicate values of the saved electrical and/or chemical characteristics. Additionally, the implant circuitry may compare the saved electrical and/or chemical characteristics over time and generate the signaling based on a threshold change in the saved electrical and/or chemical characteristics over a period of time. For example, saved electrical and/or chemical characteristics may indicate a pH level measured by a sensor electrode. Over a period of time if the sensor electrode measures a threshold change (e.g., a threshold increase in the pH level), then the implant circuitry may generate the signaling based on this threshold change occurring.

In some embodiments, the electrode array further includes at least one reference electrode (e.g., reference electrode 420), and the implant circuitry is further operative to supply voltage to the at least one reference electrode while measuring electrical and/or chemical characteristics through the reference electrode, and communicate signaling indicating the electrical and/or chemical characteristics through the at least one reference electrode through the wireless communication interface. Additionally or alternatively, in some embodiments, the implant circuitry is further operative to compare the electrical and/or chemical characteristics through the at least one reference electrode and the electrical and/or chemical characteristics through the sensor electrodes, and generate the signaling to indicate the presence of the biofilm and/or indicate the electrical and/or chemical characteristics through the at least one reference electrode and the sensor electrodes, based on the electrical and/or chemical characteristics through the at least one reference electrode having at least a threshold difference from the electrical and/or chemical characteristics through the sensor electrodes.

In some embodiments, the signaling is sent from the mobile device 810 to the cloud server 910. The signaling from the mobile device to the cloud server may include at least the electrical and/or chemical characteristics, the charge status of the energy storage device, and some patient reported data (e.g., information a patient inputs into the patient app 920). For example, the data from the app (including indications in the signaling) may be uploaded from the patient's mobile device 810 to a secure cloud server 910 via internet connection such as WiFi or cellular communications such as 5G or LTE. Data may be processed on the patient's mobile device 810 prior to upload or on the cloud server 910 after upload. After processing, the data can then be accessed by the patient 800 via their patient app 920 and by the clinician via a dedicated clinician dashboard 930.

It is noted that the mobile device 810 may alternatively be a relay device or a power transmission device (e.g., power transmission device of FIGS. 10 and 11) that is used to receive the signaling from the wireless communication interface of the medical implant and transmit the signaling to a computing device for the clinician to view the signaling and generate commands regarding treatment or other control of the medical device. The clinician dashboard 930 may be displayed to the clinician on the computing device.

In some embodiments, the computing device includes a wireless communication interface operative to receive, from the medical implant, signaling based on the measured electrical and/or chemical characteristics through the sensor electrodes spaced apart on the component of the medical implant. The computing device may further include circuitry operative to detect presence of a biofilm and a location of the biofilm on the medical implant based on the received signaling, and transmit a message (e.g., treatment activation signal) that identifies stimulation electrodes, that are associated with the determined location of the biofilm, on the medical implant that are to be stimulated by current supplied by the implant circuitry to be at a level which reduces the biofilm.

In some embodiments, the location of the biofilm may be indicated by (correspond to) a zone in an electrode array, an electrode array, and/or a placement of the electrode array on a component of the medical implant.

In some embodiments, the circuitry of the computing device is further operative to generate the message to indicate duration and/or level of stimulation for the identified stimulation electrodes based on the received electrical and/or chemical characteristics.

In some embodiments, the circuitry of the computing device is further operative to detect the presence of the biofilm based on a trend over time of the received electrical and/or chemical characteristics. For example, the circuitry may detect the presence of the biofilm based on a pH level and/or impedance changing over time.

In some embodiments, the circuitry is further operative to determine a type of bacteria in the biofilm based on the signaling from the medical implant. The circuitry can determine duration and/or level of stimulation based on the determined type of bacteria, and can generate the message to indicate the duration and/or level of stimulation for the identified stimulation electrodes.

For example, the message (e.g., a treatment activation signal), that identifies at least one of the stimulation electrodes of the medical implant to be electrically stimulated, may be uploaded to the cloud server 910 and then accessed or obtained by the mobile device 810. The mobile device may then transmit the message to the medical device.

However, it should be noted that in some embodiments, the implant circuitry may be operative to perform the operations of the computing device.

In some embodiments, the electrode array of the medical implant further includes stimulation electrodes spaced apart on the implant component, and the implant circuitry is further operative to receive the message, through the wireless communication interface, identifying at least one of the stimulation electrodes to be electrically stimulated, and electrically stimulate the at least one of the stimulation electrodes identified by the received message.

Figure 10:
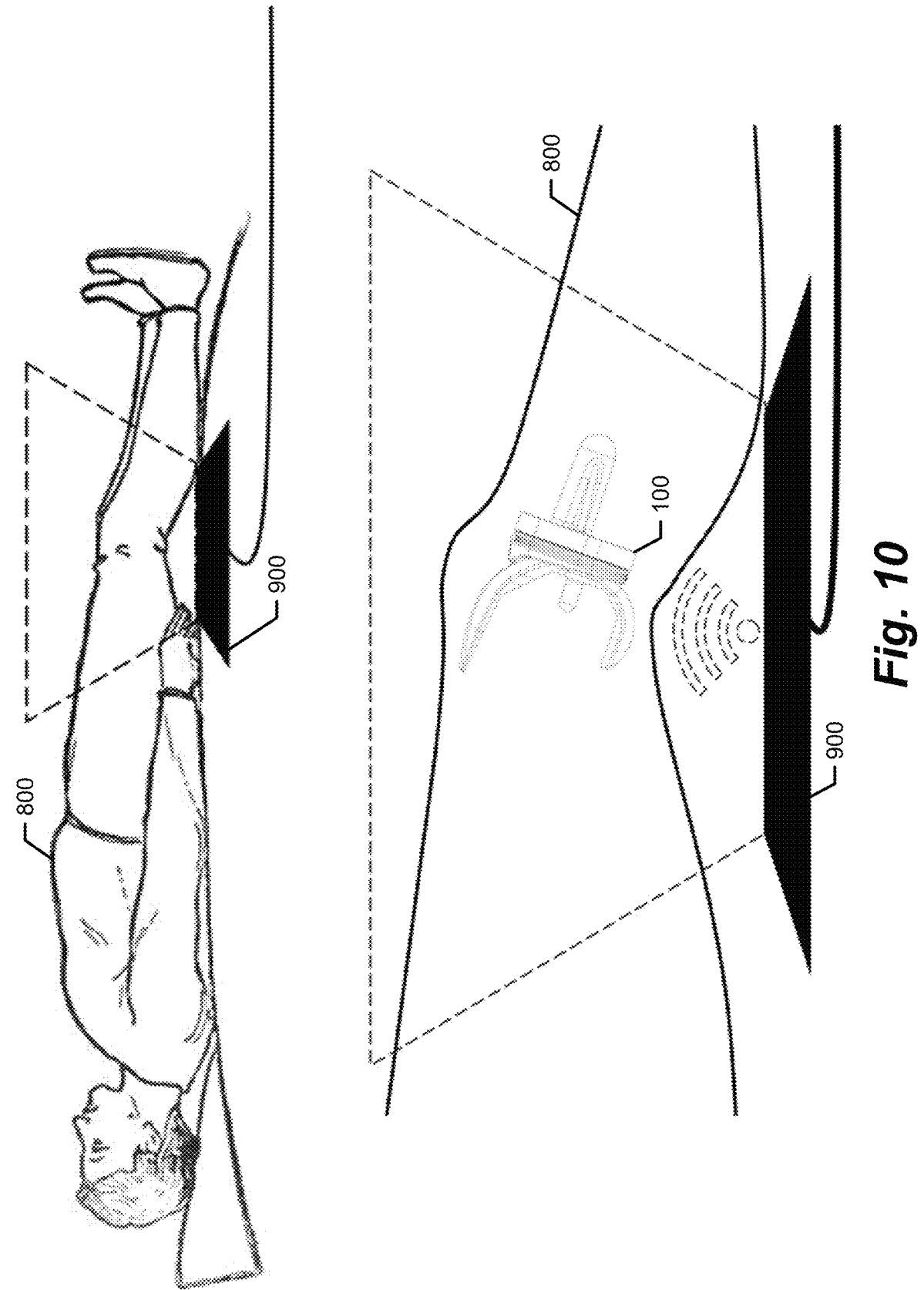
FIG. 10 illustrates the patient with the medical implant that is implanted in the patient and is configured to wirelessly receive radio frequency (RF) signals from a power transmitter device and charge the energy storage device from the received RF signals, according to some embodiments of the present disclosure.

FIG. 10 illustrates the patient 800 with the medical implant 100 that is implanted in the patient 800 and is configured to wirelessly receive radio frequency (RF) signals from a power transmitter device 900 and charge the energy storage device (e.g., energy storage device 130) of the medical implant from the received RF signals, according to some embodiments of the present disclosure.

Figure 11:
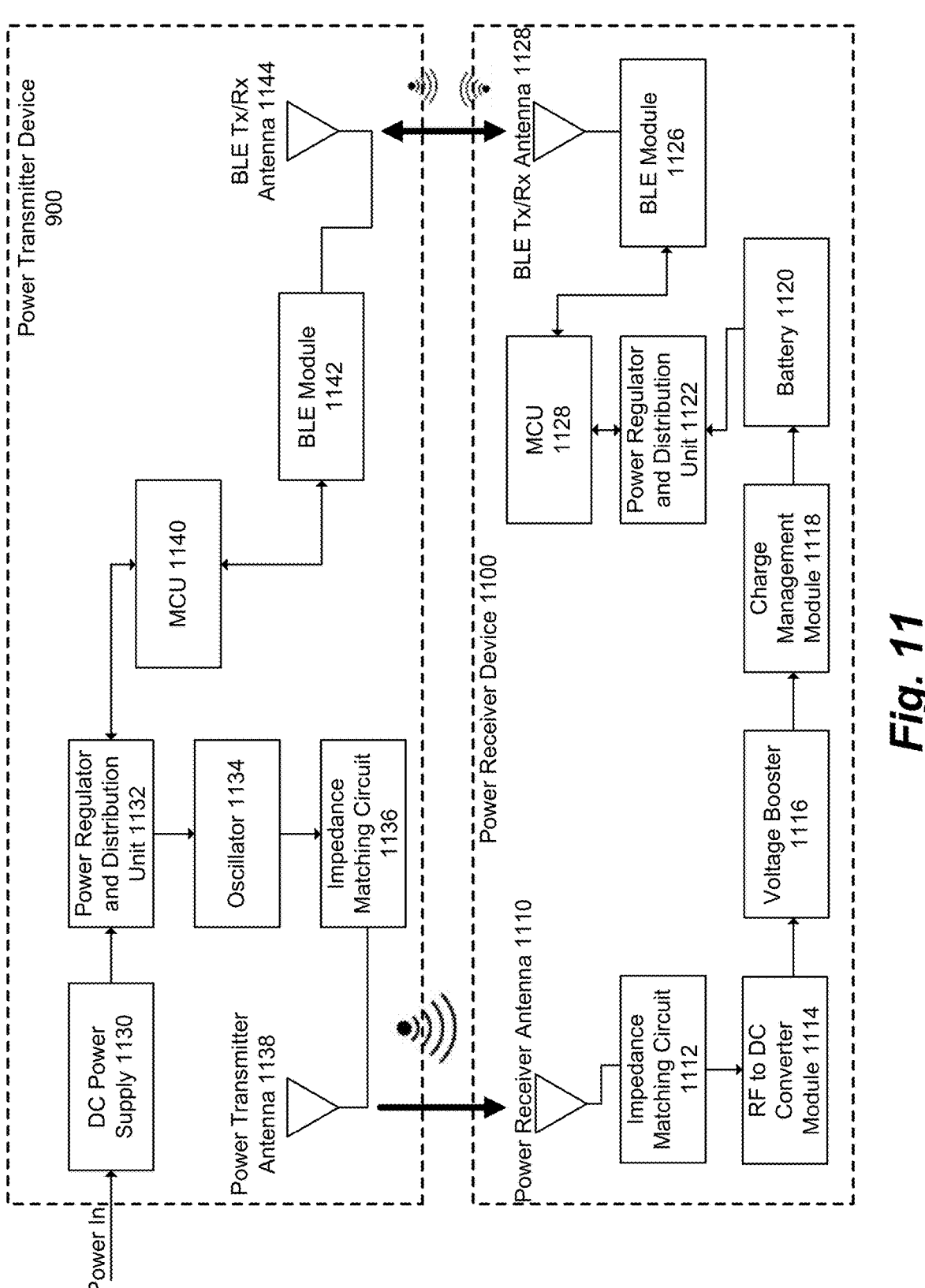
FIG. 11 illustrates a block diagram of a power receiver device of the medical implant and a power transmitter device where the power receiver device is configured to receive, from the power transmitter device, RF signals to allow for wireless charging of the medical implant and receive/transmit other signals to the power transmitter device, according to some embodiments of the present disclosure.

FIG. 11 illustrates a block diagram of a power receiver device 1100 of the medical implant and the power transmitter device 900 where the power receiver device 1100 is configured to receive, from the power transmitter device 900, RF signals to allow for wireless charging of the medical implant and receive/transmit other signals to the power transmitter device 900, according to some embodiments of the present disclosure In some embodiments, a power receiver circuitry (e.g., power receiver device 1100) that wirelessly receives radio frequency (RF) signals from a power transmitter device (e.g., power transmitter device 900) that is separate from the medical implant 100, converts the received RF signals to direct current (DC) power, and charges the energy storage device (e.g., energy storage device 130) with the DC power.

Referring to the examples of FIGS. 10 and 11, the medical implant 100 is powered by an integrated rechargeable battery (e.g., energy storage device 130). The battery is recharged via an automated RF-based wireless charging system. The charging system includes a power receiver device 1100 embedded within the medical implant and an power transmitter device 900.

The power transmitter device 900 contains a signal antenna (e.g., BLE Transmission (Tx)/Reception (Rx) Antenna 1144) and power transmitter antenna 1138, which may operate on the same or different frequencies. For example, the signal antenna might operate at 2.4 GHz to facilitate communication with the medical implant and mobile device via Bluetooth® while the power transmitter antenna 1138 operates at 915 MHz. The signal antenna and power transmitter antenna 1138 are connected to a microcontroller (MCU) 1140 or other processor unit within the device.

In some embodiments the electronic components of the power transmitter device 900 are housed in a pad-like form factor to enable the patient 800 to place the power transmitter device 900 on top of their mattress or preferred seating area. The antennas within the power transmitter device 900 are designed for directional transmission normal to the plane of the pad as shown by the dotted lines in FIG. 10. Additionally, the antennas form a coverage volume to facilitate charging of the medical implant while the patient 800 is lying down or seated in various positions.

The medical implant may include a signal antenna (e.g., BLE Tx/Rx antenna 1128) and power receiver antenna 1110, which may operate on the same or different frequencies. For example, the signal antenna might operate at 2.4 GHz to facilitate communication with the power transmitter device 900 and mobile device (e.g., mobile device 810) via Bluetooth® while the power receiver antenna 1110 operates at 915 MHz. Power received by the power receiver antenna 1110 is converted to DC and then passed to a charging module to charge the battery (discussed in more detail below).

In some embodiments, the power receiver device 1100 of the medical implant is within the implant component (e.g., implant component 150) or is separate from the implant component.

In other embodiments, the electronic components of the power transmitter device 900 are housed in a medical brace-like form factor (e.g., a knee brace, leg brace, wrist brace, etc) to enable the patient to wear the power transmitter device 900.

In preferred embodiments, the power transmitter device 900 receives power from a wall outlet, however, in some embodiments the power transmitter device 900 also includes a battery that allows the power transmitter device 900 to be more mobile and receive the power from the battery.

Referring to FIG. 11, for power transfer from the power transmitter device 900 to the power receiver device 1100, the DC power supply 1130 receives power from an external power source (e.g., wall outlet) and sends the power to a power regulator and distribution unit 1132. The power regulator and distribution unit 1132 regulates the power received by the power transmitter device 900 and distributes the power to a MCU 1140 and/or oscillator 1134. The oscillator 1134 oscillates the power into a signal (e.g., RF signal) and sends the signal to an impedance matching circuit 1136 that performs impedance matching operations to help maximize the power transfer to the power receiver device 1100. The impedance matching circuit then sends the impedance matched signal (through power transmitter antenna 1138) to a power receiver antenna 1110 of the power received device 1100.

The power receiver antenna 1110 receives the power signal and sends the power signal to the impedance matching circuit 1112, which then sends the signal to a RF to DC converter module 1114. The RF to DC converter module 1114 converts the power signal from RF signals to DC power and sends this DC power to the voltage booster 1116. The voltage booster 1116 boosts the DC power voltage and sends the voltage boosted DC power to the charge management module 1118, which then sends the power to the battery 1120.

For communications (e.g., BLE communications) from the power transmitter device 900 to the power receiver device 1100, the MCU 1140 receives power from the power regulator and distribution unit 1132 and sends signals (e.g., treatment activation signal(s)) to the BLE module 1142, which sends signals (through the BLE Tx/Rx antenna 1144) to a BLE Tx/Rx antenna 1128 of the power receiver device 1100.

For communications (e.g., BLE communications) from the power receiver device 1100 to the power transmitter device 900, the battery 1120 sends power to the power regulator and distribution unit 1122, which then sends the power to the MCU 1128. The MCU 1128 sends a signal(s) (e.g., signaling indicating electrical and/or chemical characteristics) to the BLE module 1126 which transmits, through the BLE Tx/Rx antenna 1128 the signal(s) to the BLE Tx Rx antenna 1144 of the power transmitter device 900.

In some embodiments, the power transmitter device 900 may act as a relay device that receives these signals from the power receiver device 1100 or another wireless communication interface and upload the signals to a cloud server (e.g., cloud server 910 of FIG. 9).

Figure 13:
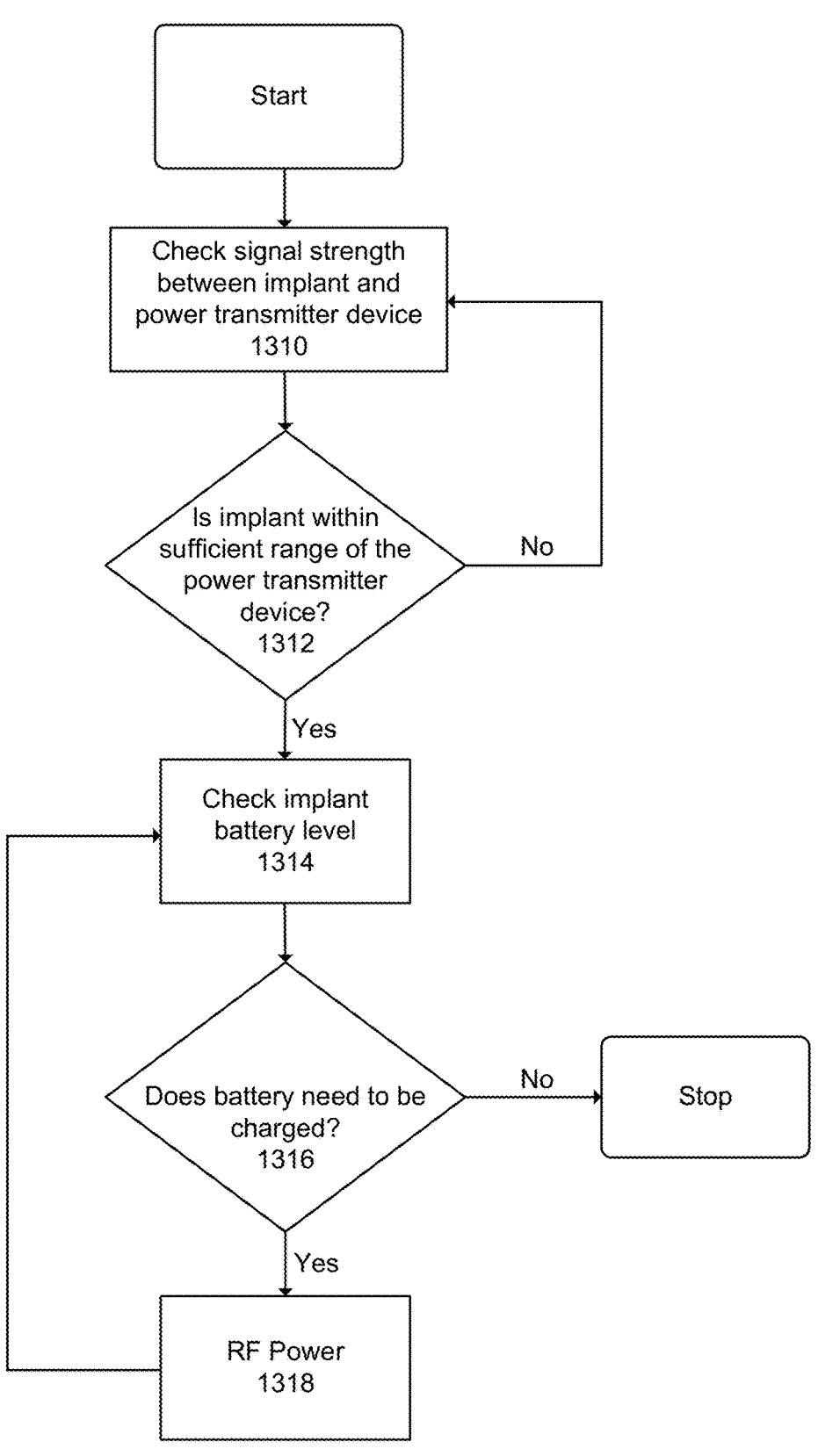
FIG. 13 illustrates a block diagram of wireless charging operations performed by the medical implant and/or power transmitter device, according to some embodiments of the present disclosure.

FIG. 13 illustrates a block diagram of wireless charging operations performed by the medical implant and/or power transmitter device, according to some embodiments of the present disclosure. In some embodiments, the operations are performed by the medical implant (e.g., implant circuitry 156). In other embodiments, the operations are performed by the MCU 1140 of the power transmitter device 900.

The operation of FIG. 13 are directed to an automated charging algorithm that recharges the energy storage device of the medical implant as needed without intervention from the patient. The patient may only need to ensure that the power transmitter device is plugged into a wall outlet for power.

When the medical implant performs the operations of FIG. 13, in operation 1310, the medical implant checks the signal strength between the medical implant and the power transmitter device. The medical implant then, in operation 1312, determines if the implant is within sufficient range of the power transmitter device. If not within sufficient range, then the medical implant returns to operation 1310. If the medical implant is within sufficient range, then the medical implant moves to operation 1314. In operation 1314, the medical implant checks the medical implant's battery level. The medical implant then, in operation 1316, determines if the battery needs to be charged. This determination may be based on the medical implant's batter level being below a threshold value. If the medical implant determines that the battery does not need to be charged, the medical implant stops the operations of FIG. 13. If the medical implant determines that the battery needs to be charged, then the medical implant moves to operation 1318 and receives RF power transmissions from the power transmitter device. As the medical implant receives the RF power transmission, the medical implant (at least periodically) performs operations 1314 through 1318.

When the power transmitter device performs the operations of FIG. 13, in operation 1310, the power transmitter device checks the signal strength between the medical implant and the power transmitter device. Then, in operation 1312, the power transmitter device determines if the medical implant is within sufficient range of the power transmitter device. If the medical implant is not within sufficient range, then the power transmitter returns to operation 1310. If the medical implant is within sufficient range, the power transmitter moves to operation 1314. In operation 1314, the power transmitter device checks the medical implant's batter level by transmitting a batter level request to the medical implant and the power transmitter receiving a battery level response from the medical implant that includes an indication of the medical implant's battery level. Then in operation 1316, the power transmitter device determines if the battery of the medical implant needs to be charged. If the battery does not need to be charged, then the operations of FIG. 13 stop. If the battery needs to be charged, then the power transmitter device moves to operation 1318, where the power transmitter device then transmits RF power to the medical implant. As the power transmitter device transmits the RF power, the power transmitter device (at least periodically) performs operations 1314 through 1318.

Figure 12:
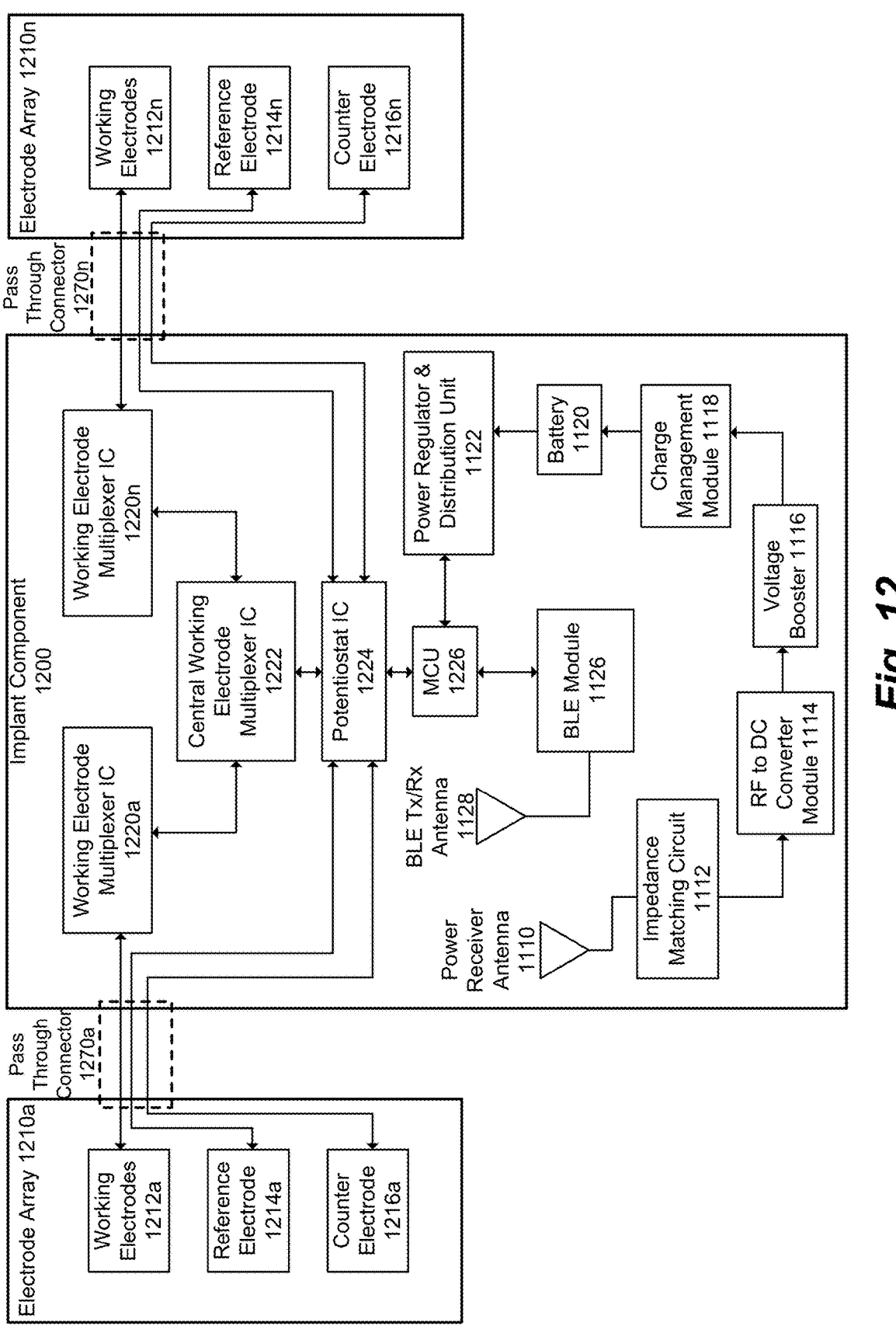
FIG. 12 illustrates components of the implant component and communications to/from the electrode arrays of the implant component, according to some embodiments of the present disclosure.

FIG. 12 illustrates components of the implant component and communications to/from the electrode arrays of the implant component, according to some embodiments of the present disclosure.

The illustrated configuration of FIG. 12 includes one or more electrode arrays (electrode arrays 1210*a-n*) on the surface of the implant component. Each electrode array may include one or more working electrodes (e.g., working electrodes 1212*a-n*), a reference electrode (e.g., reference electrode 1214*a-n*), and a counter electrode (e.g., counter electrode 1216*a-n*). Each electrode is electrically connected to the implant component via pass through connectors at an interface of the implant component. Working Electrodes 1212*a-n* are internally routed to a dedicated multiplexer integrated circuit (IC) 1220*a-n*. For configurations involving more than one electrode array, each electrode array may have a dedicated multiplexer that is connected to a central multiplexer (central working electrode multiplexer IC

1222). The central working electrode multiplexer IC 1222 is connected to the potentiostat IC 1224, which performs the electrochemical signal output and processing of signal responses. The multiplexers enable switching of connections between individual working electrodes and the single potentiostat IC 1224. Otherwise an individual potentiostat IC would be required for each working electrode. The reference and counter electrodes of each electrode array may also be connected to the potentiostat IC to complete the 3-electrode system. The potentiostat IC is connected to the MCU 1226, which may be the primary processor for the entire system. The remaining power and communication elements of the implant component are described with reference to Figure above.

While a single potentiostat IC is used herein, a plurality of potentiostat may be used. For example, there may be a potentiostat IC for each electrode array.

The implant component of FIG. 12 may also be used to deliver electric stimulation to prevent and/or eradicate biofilm on the surface of the medical implant. In general, a potentiostat is the electronic hardware required to control a three-electrode cell for electrochemical experiments. Depending on the application, a potentiostat can be used to supply constant DC current or constant DC voltage to the electrodes. In electrochemical impedance spectroscopy applications, a potentiostat can also be used to supply AC potential at a fixed frequency or across a defined range of frequencies. Each of these potentiostat modalities could be used to supply AC and/or DC electric stimulation to the electrodes on the surface of the medical implant. Rather than supplying signals and recording the results as in electrochemical sensing, the focus of electric stimulation may be on the output signal from the circuit. In some embodiments, the same sets and arrays of electrodes used in measuring electrical and/or chemical characteristics may be used for electric stimulation. In some alternative embodiments, the implant component may include dedicated arrays, sets, or individual electrodes for the purpose of stimulation.

One possible clinical application of electric stimulation is to generate controlled concentrations of biocidal molecules, such as HOCl (hypochlorous acid), at electrode surfaces beneath or adjacent to bacterial biofilms on the medical implant. HOCl is naturally produced by white blood cells when combatting bacteria in humans and is commonly used as a wound cleansing agent in clinical settings. In low, controlled concentrations HOCl can kill bacteria and eradicate bacterial biofilms without cytotoxic effects to the surrounding tissue. In one embodiment, the medical implant could stimulate the electrodes on the surface of the implant at a constant voltage between 1.2V to 1.7V to generate low concentrations (1-50 uM) of HOCl at the interface of the electrodes and synovial fluid and/or electrodes and biofilm. The stimulation could be applied for a fixed amount of time, such as 1-3 hours, or until the sensor electrodes no longer detect the presence of the biofilm. In addition, some electrodes in the electrode array may be configured to measure the concentration of HOCl. These electrodes may be used to create an additional feedback loop (as similarly discussed above) to precisely control the concentration of generated HOCl to remain below cytotoxic limits. This feedback loop may also be used to ensure that a sufficient concentration of HOCl is generated as the concentration of chloride ions and pH level may impact the voltage required to achieve the target HOCl concentration.

Further Definitions and Embodiments

It should be noted that the use of the term "characteristic" and "parameter" may be used interchangeably.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other clement or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another clement/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A system for detecting and treating infection, comprising:

a remote computing device including:

a wireless communication circuit operative to receive, from a medical implant, signaling based on a measured electrical and/or chemical characteristics through sensor electrodes spaced apart on an implant component of the medical implant; and

a processing circuit operative to detect presence of a biofilm and a location of the biofilm on the medical implant based on the received signaling, and transmit a message that identifies stimulation electrodes, that are associated with the determined location of the biofilm, on the implant component of the medical implant that are to be stimulated by current supplied by implant circuitry at a level which reduces the biofilm, the medical implant including:

the implant component;

the sensor electrodes spaced apart on the implant component;

an energy storage device within the implant component;

a wireless communication interface within the implant component, configured to communicate with the wireless communication circuit of the remote computing device; and implant circuitry within the implant component and operative to supply voltage to at least one of the sensor electrodes to measure characteristics associated with when a biofilm is forming on the implant component, and communicate signaling indicating the electrical and/or chemical characteristics through the wireless communication interface for receipt by the wireless communication circuit, the implant circuitry, under control of he processing circuit, is further operative to electrically stimulate at least one of the stimulation electrodes by current supplied by the energy storage device to be at a level which reduces the biofilm on at least part of the implant component while implanted in the patient, wherein the implant circuitry, under control of the processing circuit, is further operative to control the current supplied by the energy storage device to the stimulation electrodes to be a level sufficient to form hydrogen bubbles through reaction with patient fluid and dislodge the biofilm and/or to change potential hydrogen (PH) of the patient fluid to a level which reduces the biofilm, the implant circuitry, under control of the processing circuit, is further operative to control the current supplied by the energy storage device to the stimulation electrodes to be a level sufficient to form hydrogen bubbles through reaction with patient fluid and dislodge the biofilm and/or to change potential hydrogen (PH) of the patient fluid to a level which reduces the biofilm.

2. The system of claim 1, wherein:

the processing circuit is further operative to detect the presence of the biofilm based on a trend over time of the received electrical and/or chemical characteristics.

3. The system of claim 1, wherein:

the processing circuit is further operative to generate the message to indicate duration and/or level of stimulation for the identified stimulation electrodes based on the received electrical and/or chemical characteristics.

4. The system of claim 1, wherein:

the processing circuit is further operative to determine a type of bacteria in the biofilm based on the signaling from the medical implant, determine duration and/or level of stimulation based on the determined type of bacteria, and

generate the message to indicate the duration and/or level of stimulation for the identified stimulation electrodes.

5. The system of claim 1, wherein:

the implant circuitry is further operative to determine presence of the biofilm based on the electrical and/or chemical characteristics, and generate the signaling to indicate the presence of the biofilm and/or indicate the electrical and/or chemical characteristics, based on the determined presence of the biofilm.

6. The system of claim 5, wherein:

the implant circuitry is further operative to generate the signaling to further indicate locations on the implant component that correspond to where the electrical and/or chemical characteristics indicate the presence of the biofilm.

7. The system of claim 5, wherein:

the medical implant includes the stimulation electrodes spaced apart on the implant component, and the implant circuitry, under control of the remote computing device, is further operative to electrically stimulate at least one of the stimulation electrodes on a part of the implant component associated with the biofilm by supplying current from the energy storage device at a level which reduces the biofilm.

8. The system of claim 7, wherein:

the implant circuitry, under control of the remote computing device, is further operative to control the duration and/or level of stimulation of the stimulation electrodes based on the detected type of bacteria.

9. The system of claim 1, wherein the medical implant further comprises:

a power receiver circuitry that wirelessly receives radio frequency (RF) signals from the wireless communication circuit, converts the received RF signals to direct current (DC) power, and charges the energy storage device with the DC power.

10. The system of claim 1, wherein:

the electrical and/or chemical characteristics of the sensor electrodes indicate at least one of impedance, conductivity, and potential hydrogen (pH).

11. The system of claim 1, wherein:

the implant circuitry, under control of the processing circuit, is further operative to simultaneously measure the electrical and/or chemical characteristics through the sensor electrodes and to electrically stimulate the stimulation electrodes.

12. The system of claim 11, wherein:

the implant circuitry is further operative to increase or decrease the current supplied by the energy storage device to the stimulation electrodes responsive to the electrical and/or chemical characteristics.

13. The system of claim 1, wherein:

the sensor arrays include at least one reference electrode, and the implant circuitry is further operative to supply voltage to the at least one reference electrode while measuring electrical and/or chemical characteristics through the reference electrode, and communicate signaling indicating the electrical and/or chemical characteristics through the at least one reference electrode through the wireless communication interface.

14. The system of claim 13, wherein:

the implant circuitry is further operative to compare the electrical and/or chemical characteristics through the at least one reference electrode and the electrical and/or chemical characteristics through the sensor electrodes, and generate the signaling to indicate the presence of the biofilm and/or indicate the electrical and/or chemical characteristics through the at least one reference electrode and the sensor electrodes, based on the electrical and/or chemical characteristics through the at least one reference electrode having at least a threshold difference from the electrical and/or chemical characteristics through the sensor electrodes.

15. The system of claim 1, wherein:

the one of the sensor electrodes includes a coating of a bio-recognition element adapted to bind to a type of bacterial species.

16. The system of claim 1, wherein:

the implant circuitry is further operative to supply a defined range of frequencies to the sensor electrodes to measure electrical and/or chemical characteristics, wherein the defined range of frequencies is adapted to electrically excite one or more types of bacterial species.

17. The system of claim 1, wherein:

the sensor electrodes comprise a first zone of at least one sensor electrode of the sensor electrodes and a second zone of at least one electrode of the sensor electrodes, wherein the first zone and second zone are separate, and the implant circuitry is further operative to compare the electrical and/or chemical characteristics from the at least one sensor electrode in the first zone to the electrical and/or chemical characteristics of the second zone, and generate the signaling to indicate the presence of the biofilm and/or indicate the electrical and/or chemical characteristics from the at least one sensor electrodes in the first zone and second zone, based on the electrical and/or chemical characteristics from the at least one sensor electrode in the first zone being a threshold difference from the electrical and/or chemical characteristics from the at least one sensor electrode in the second zone.

* * * * *